(12) United States Patent
Schulze zur Wiesche

(10) Patent No.: US 9,066,892 B2
(45) Date of Patent: *Jun. 30, 2015

(54) HAIR TREATMENT AGENTS CONTAINING 4-MORPHOLINO-METHYL-SUBSTITUTED SILICONE(S) AND THICKENING AGENT(S)

(71) Applicant: Henkel AG & Co. KGaA, Duesseldorf (DE)

(72) Inventor: Erik Schulze zur Wiesche, Hamburg (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/291,228

(22) Filed: May 30, 2014

(65) Prior Publication Data

US 2015/0023901 A1  Jan. 22, 2015

Related U.S. Application Data

(63) Continuation of application No. PCT/EP2012/072224, filed on Nov. 9, 2012.

(30) Foreign Application Priority Data

Dec. 2, 2011 (DE) .......... 10 2011 087 621

(51) Int. Cl.
  *A61Q 5/00* (2006.01)
  *A61K 8/898* (2006.01)
  *A61Q 5/12* (2006.01)
  *A61Q 5/02* (2006.01)

(52) U.S. Cl.
  CPC ........... *A61K 8/898* (2013.01); *A61Q 5/004* (2013.01); *A61Q 5/12* (2013.01); *A61K 2800/48* (2013.01); *A61Q 5/02* (2013.01)

(58) Field of Classification Search
  CPC ............ A61Q 5/06; A61Q 5/12; A61Q 5/04; A61K 8/25; A61K 8/585; A61K 8/898
  USPC ................. 424/70.122, 70.13, 489
  See application file for complete search history.

(56) References Cited

U.S. PATENT DOCUMENTS

| | | | |
|---|---|---|---|
| 6,007,801 A | 12/1999 | Hossel et al. | |
| 6,117,420 A | 9/2000 | Kuwata et al. | |
| 6,824,764 B2* | 11/2004 | Devin-Baudoin et al. | ... 424/70.1 |
| 2006/0258820 A1 | 11/2006 | Schneider et al. | |
| 2008/0107815 A1 | 5/2008 | Schneider et al. | |
| 2014/0305464 A1* | 10/2014 | Degeorge et al. | ............. 132/208 |

FOREIGN PATENT DOCUMENTS

WO  2013/014140 A2  1/2013

OTHER PUBLICATIONS

STIC Search Report dated Oct. 21, 2014.*
PCT International Search Report (PCT/EP2012/072224) dated Apr. 24, 2014.
PCT International Preliminary Report on Patentability (PCT/EP2012/072224) dated Jul. 8, 2014.
"Kosmetische Zusammensetzungen"; IP.com Journal; IP.com Inc., West Henrietta, NY, US; Aug. 4, 2011; XP013146799; ISSN: 1533-0001.

* cited by examiner

*Primary Examiner* — Eisa Elhilo
(74) *Attorney, Agent, or Firm* — David K. Benson

(57) ABSTRACT

Cosmetic compositions include in a cosmetically acceptable medium at least one thickening agent and at least one 4-morpholino-methyl-substituted silicone of formula (V), in which A represents structural unit (I), (II) or (III) or an O-bound oligomeric or polymeric radical including structural units of formulae (I), (II) or (III) or half of a connecting O-atom to a structural unit (III) or represents —OH; wherein * represents a bond to one of the structural units (I), (II) or (III) or an end group B (Si-bound) or D (O-bound); B represents a group —O—Si(CH$_3$)$_3$, —O—Si(CH$_3$)$_2$OH, —O—Si(CH$_3$)$_2$OCH$_3$; D represents a group —Si(CH$_3$)$_3$, —Si(CH$_3$)$_2$OH, —Si(CH$_3$)$_2$OCH$_3$; a, b and c represent integers between 0 and 1000, with the proviso a+b+c>0; m, n and o represent integers between 1 and 1000.

16 Claims, No Drawings

SEQUENCE LISTING

```
<160> NUMBER OF SEQ ID NOS: 8

<210> SEQ ID NO 1
<211> LENGTH: 3
<212> TYPE: PRT
<213> ORGANISM: Artificial
<220> FEATURE:
<223> OTHER INFORMATION: Peptide

<400> SEQUENCE: 1

Glu Glu Glu
1

<210> SEQ ID NO 2
<211> LENGTH: 4
<212> TYPE: PRT
<213> ORGANISM: Artificial
<220> FEATURE:
<223> OTHER INFORMATION: Peptide

<400> SEQUENCE: 2
```

Tyr Glu Glu Glu
1

<210> SEQ ID NO 3
<211> LENGTH: 4
<212> TYPE: PRT
<213> ORGANISM: Artificial
<220> FEATURE:
<223> OTHER INFORMATION: Peptide

<400> SEQUENCE: 3

Glu Glu Glu Ile
1

<210> SEQ ID NO 4
<211> LENGTH: 6
<212> TYPE: PRT
<213> ORGANISM: Artificial
<220> FEATURE:
<223> OTHER INFORMATION: Peptide

<400> SEQUENCE: 4

Tyr Glu Glu Glu Ile Arg
1               5

<210> SEQ ID NO 5
<211> LENGTH: 7
<212> TYPE: PRT
<213> ORGANISM: Artificial
<220> FEATURE:
<223> OTHER INFORMATION: Peptide

<400> SEQUENCE: 5

Tyr Glu Glu Glu Ile Arg Val
1               5

<210> SEQ ID NO 6
<211> LENGTH: 8
<212> TYPE: PRT
<213> ORGANISM: Artificial
<220> FEATURE:
<223> OTHER INFORMATION: Peptide

<400> SEQUENCE: 6

Tyr Glu Glu Glu Ile Arg Val Leu
1               5

<210> SEQ ID NO 7
<211> LENGTH: 9
<212> TYPE: PRT
<213> ORGANISM: Artificial
<220> FEATURE:
<223> OTHER INFORMATION: Peptide

<400> SEQUENCE: 7

Leu Tyr Glu Glu Glu Ile Arg Val Leu
1               5

<210> SEQ ID NO 8
<211> LENGTH: 5
<212> TYPE: PRT
<213> ORGANISM: Artificial
<220> FEATURE:

```
<223> OTHER INFORMATION: Peptide

<400> SEQUENCE: 8

Tyr Glu Glu Glu Ile
1               5
```

HAIR TREATMENT AGENTS CONTAINING 4-MORPHOLINO-METHYL-SUBSTITUTED SILICONE(S) AND THICKENING AGENT(S)

FIELD OF THE INVENTION

The present invention generally relates to hair treatment agents that include specially substituted silicone(s), and to the use of said agents for cleaning and/or caring for hair.

BACKGROUND OF THE INVENTION

Care-providing agents for keratinic fibers influence the natural structure and properties of hair. Subsequent to such treatments, for example, the wet and dry combabiity of the hair, and its hold and fullness, can be optimized, or the hair can be protected from increased splitting. It has therefore been usual for some time to subject the hair to a special post-treatment. In this the hair is treated, usually in the form of a rinse, with special active agents, for example quaternary ammonium salts or special polymers. Depending on the formulation, this treatment improves the combability, hold, and fullness of the hair, increases shine, and decreases the splitting rate.

In addition, more recently so-called combination preparations have been developed in order to reduce the complexity of the usual multi-step methods, in particular in a context of direct application by users. These preparations additionally include, besides the usual components e.g. for cleaning the hair, active agents that were once reserved for hair post-treatment agents. One utilization step for the consumer is thus eliminated, and at the same time the packaging complexity is reduced because one fewer product is used.

The known active agents cannot, however, meet all requirements to a sufficient extent. A demand therefore continues to exist for active agents or active-agent combinations for cosmetic agents having good care-providing properties and good biodegradability. In surfactant- and/or electrolyte-containing formulations in particular, a demand exists for additional care-providing active agents, which can be incorporated without difficulty into known formulations and whose effect is not attenuated as a result of incompatibilities with other ingredients.

Silicones, and among them aminofunctional silicones, are known as care-providing agents in hair treatment agents, and corresponding products are widespread on the market. A demand continues to exist, however, for improving the effects achieved, in particular in terms of the feel, combability, softness, and volume of the hair or hairstyle, and for decreasing the utilization quantities.

It is therefore desirable to provide silicone-containing hair treatment agents that impart to the hair treated with them even better properties than hair treatment agents having known amodimethicones. It is also desirable to achieve equivalent or better effects even with appreciably reduced utilization quantities. In particular, it is desirable for such agents to improve the feel, combability, softness, and volume of the hair or hairstyle, and to appreciably minimize the contact angle of water drops present on the treated hair, this being an indication of product performance.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A cosmetic composition including, in a cosmetically acceptable medium, at least one thickening agent and at least one 4-morpholinomethyl-substituted silicone of formula (V)

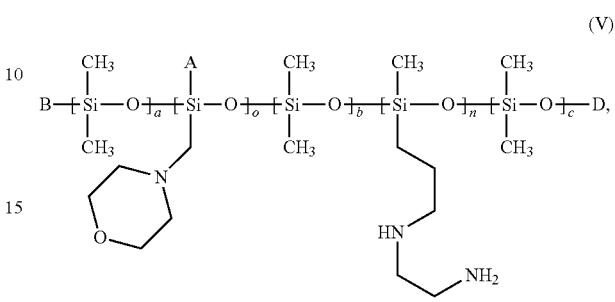

in which A denotes a structural unit (I), (II), or (III) bound via —O—

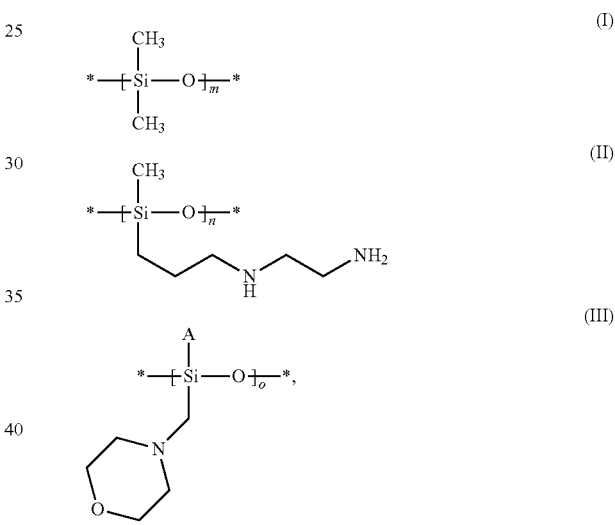

or an oligomeric or polymeric residue bound via —O— containing structural units of formulas (I), (II), or (III), or half of an oxygen atom connecting to a structural unit (III), or denotes —OH; * denotes a bond to one of the structural units (I), (II), or (III), or denotes a terminal group B (Si-bound) or D (O-bound); B denotes an —OH, —O—Si(CH$_3$)$_3$, —O—Si(CH$_3$)$_2$OH, —O—Si(CH$_3$)$_2$OCH$_3$ group; D denotes an —H, —Si(CH$_3$)$_3$, —Si(CH$_3$)$_2$OH, —Si(CH$_3$)$_2$OCH$_3$ group; a, b, and c denote integers between 0 and 1000, with the provision that a+b+c>0; and m, n, and o denote integers between 1 and 1000.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject of the present invention is a cosmetic composition containing, in a cosmetically acceptable medium, at least one thickening agent and at least one 4-morpholinomethyl-substituted silicone of formula (V)

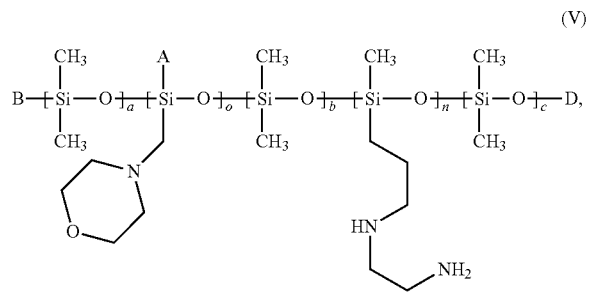

in which
A denotes a structural unit (I), (II), or (III) bound via —O—

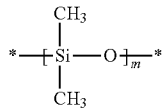

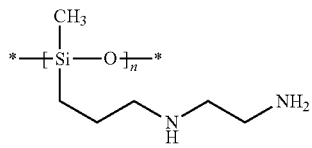

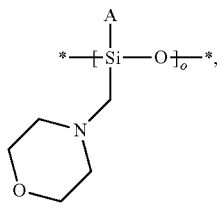

or an oligomeric or polymeric residue bound via —O— containing structural units of formulas (I), (II), or (III), or half of an oxygen atom connecting to a structural unit (III), or denotes —OH,
* denotes a bond to one of the structural units (I), (II), or (III), or denotes a terminal group B (Si-bound) or D (O-bound),
B denotes an —OH, —O—Si(CH$_3$)$_3$, —O—Si(CH$_3$)$_2$OH, —O—Si(CH$_3$)$_2$OCH$_3$ group,
D denotes an —H, —Si(CH$_3$)$_3$, —Si(CH$_3$)$_2$OH, —Si(CH$_3$)$_2$OCH$_3$ group,
a, b, and c denote integers between 0 and 1000, with the provision that a+b+c>0,
m, n, and o denote integers between 1 and 1000.

The agent according to the present invention is a cosmetic agent. Cosmetic agents preferred according to the present invention are selected from the group of shower gels, shower/bath products, dental cleaning agents, mouthwashes, hair shampoos, hair conditioners, conditioning shampoos, hair sprays, hair rinses, hair therapies, hair packs, hair tonics, permanent wave retention solutions, hair coloring shampoos, hair coloring agents, hair setting agents, hair setting products, hair styling preparations, blow-dry wave lotions, foam setting agents, hair gels, hair waxes, or combinations thereof.

Particularly preferred cosmetic agents according to the present invention serve for the treatment of keratinic fibers and thus represent hair treatment agents. "Hair treatment agents" for purposes of the present invention are, for example, hair shampoos, hair conditioners, conditioning shampoos, hair sprays, hair rinses, hair therapies, hair packs, hair tonics, permanent wave retention solutions, hair coloring shampoos, hair coloring agents, hair setting agents, hair setting products, hair styling preparations, blow-dry wave lotions, foam setting agents, hair gels, hair waxes, or combinations thereof. In view of the fact that men are often reluctant to use multiple different agents and/or multiple utilization steps, agents according to the present invention are preferably those which a man uses in any case. Preferred agents according to the present invention are therefore shampoos, conditioning agents, or hair tonics.

The compositions of the invention exhibit improved cosmetic properties (in the case of hair, for example, lightness, softness, ability to untangle, natural feel and an airy hairstyle, brightness); in addition, the effects are more persistent and durable. These effects are, in particular, resistant to many shampoos.

The compositions of the invention moreover result in improved skin suppleness upon application onto the skin (for example by way of a foam bath or shower gel).

The agents according to the present invention contain as a first essential ingredient at least one 4-morpholinomethyl-substituted silicone of the structural formula (V). The latter illustrates the fact that the siloxane groups n and o do not obligatorily need to be bound directly to a terminal grouping B or D, respectively. Instead, in preferred formulas (V) a>0 or b>0, and in particularly preferred formulas (V) a>0 and b>0, i.e. the respective terminal grouping B or D is preferably bound to a dimethylsiloxy grouping. In formula (V) the siloxane units a, b, c, n, and o also are preferably statistically distributed.

The silicones used according to the present invention and represented by formula (V) can be trimethylsilyl-terminated at both ends (D=—Si(CH$_3$)$_3$, B=—O—Si(CH$_3$)$_3$), but they can also be dimethylsilylhydroxy-terminated or dimethylsilylmethoxy-terminated at one or two ends. Silicones used particularly preferably in the context of the present invention comprise at least one terminal dimethylsilylhydroxy group, i.e. are selected from silicones in which

| | | |
|---|---|---|
| B = —O—Si(CH$_3$)$_2$OH | and | D = —Si(CH$_3$)$_3$ |
| B = —O—Si(CH$_3$)$_2$OH | and | D = —Si(CH$_3$)$_2$OH |
| B = —O—Si(CH$_3$)$_2$OH | and | D = —Si(CH$_3$)$_2$OCH$_3$ |
| B = —O—Si(CH$_3$)$_3$ | and | D = —Si(CH$_3$)$_2$OH |
| B = —O—Si(CH$_3$)$_2$OCH$_3$ | and | D = —Si(CH$_3$)$_2$OH. |

These silicones result in exorbitant improvements in the hair properties of hair treated with the agents according to the present invention, in particular in a large decrease in contact angle.

The structural units of formulas (I), (II), and (III) can be present in statistically distributed fashion in the molecule, but the silicones used according to the present invention can also be block copolymers made up of blocks of the individual structural units, wherein the blocks can in turn be present in statistically distributed fashion.

The "*" at the free valences of structural units (I), (II), or (III) denotes a bond to one of the structural units (I), (II), or (III), or denotes a terminal group B (Si-bound) or D (O-bound).

In formula (V), the residue A can denote
a structural unit (I), (II), or (III) bound via —O—, or
an oligomeric or polymeric residue bound via —O— containing structural units of formulas (I), (II), or (III), or half of an oxygen atom connecting to a structural unit (III), or can denote —OH.
Formula (V) thereby becomes refined to one of formulas (Va), (Vb), (Vc), (Vd), (Ve), or (Vf):
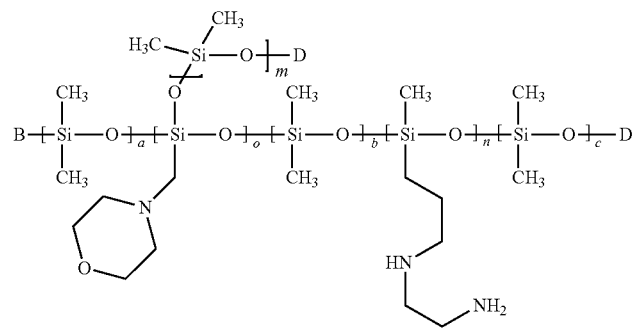
(Va)
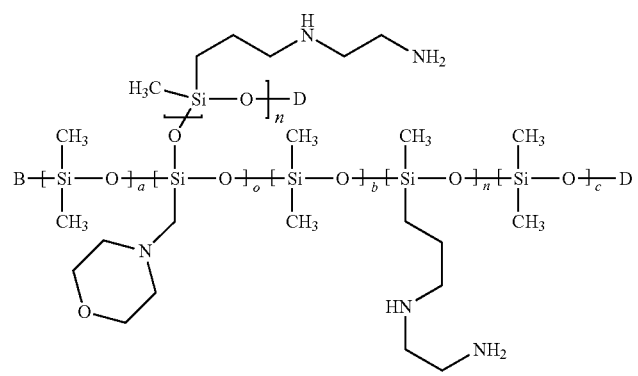
(Vb)
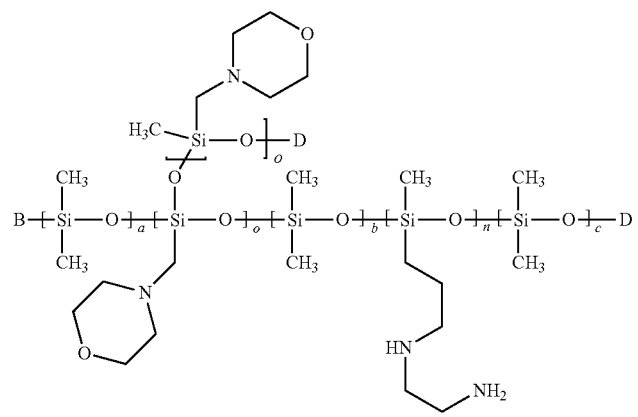
(Vc)

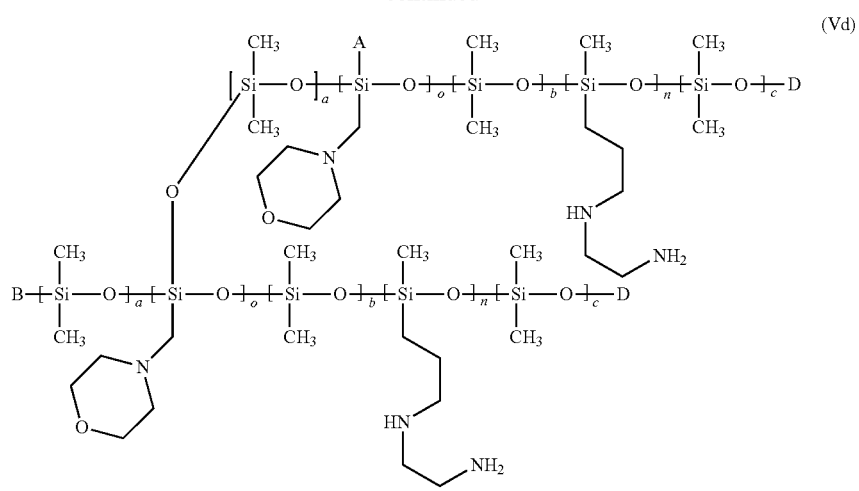
(Vd)
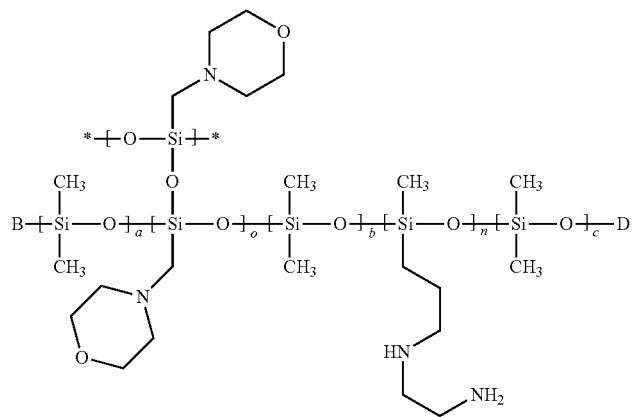
(Ve)
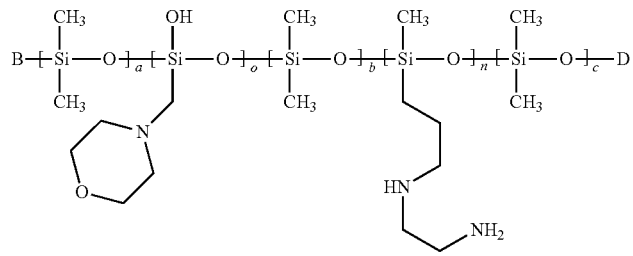
(Vf)

In structural unit (III), the residue A can denote
a structural unit (I), (II), or (III) bound via —O—, or
an oligomeric or polymeric residue bound via —O— containing structural units of formulas (I), (II), or (III), or
half of an oxygen atom connecting to a structural unit (III), or can denote —OH.

In the first case, structural unit (III) becomes one of the structural units (IIIa), (IIIb), or (IIIc):

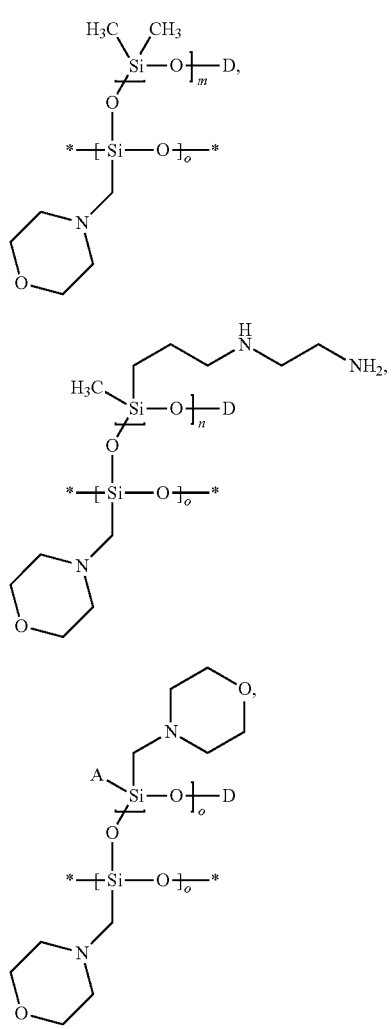

where m=n=o=1, and A and D are respectively as defined above.

In the second case, the indices m, n, and o in the formulas (IIIa), (IIIb), and (IIIc) recited above can denote integers between 2 and 1000. The second case also, however, covers oligomeric or polymeric residues that contain at least two different structural units of formulas (I), (II), or (III), as depicted in formula (IIId):

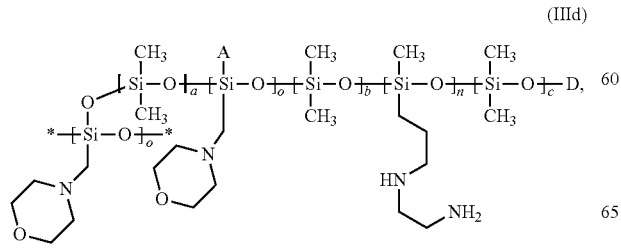

in which a, b, and c denote integers between 0 and 1000, with the provision that a+b+c>0, and n and o denote integers between 1 and 1000.

In the third case, A denotes half of an oxygen atom connecting to a structural unit (III) (depicted in structural unit (IIIe)), or denotes —OH (depicted in structural unit (IIIf)):

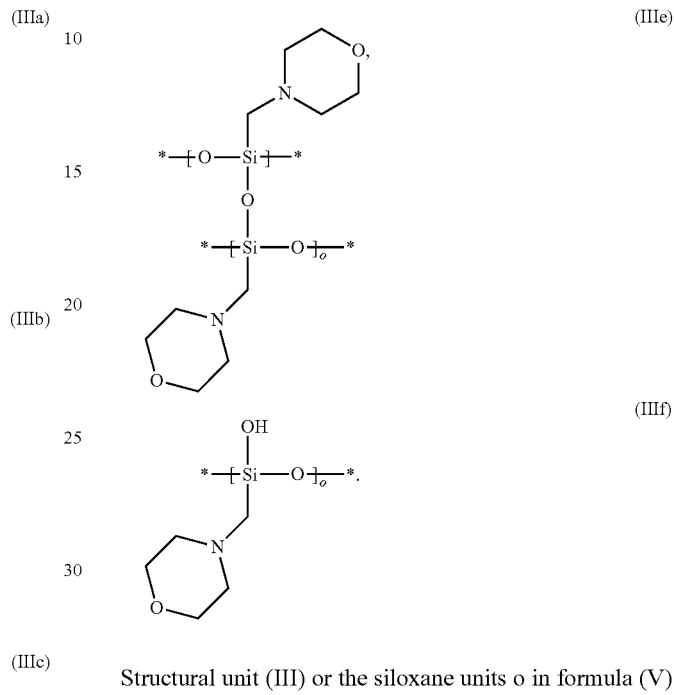

Structural unit (III) or the siloxane units o in formula (V) can constitute, via group A, nested or partial cage structures if A denotes half of an oxygen atom connecting to a structural unit (III). Hair treatment agents according to the present invention that include silicones having corresponding 4-morpholinomethyl-substituted silsesquioxane substructures are preferred according to the present invention, since these silicones result in enormously improved combability values and drastically reduced contact angles.

Cosmetic agents preferred according to the present invention are accordingly characterized in that they include at least one 4-morpholinomethyl-substituted silicone that comprises structural units of formula (VI)

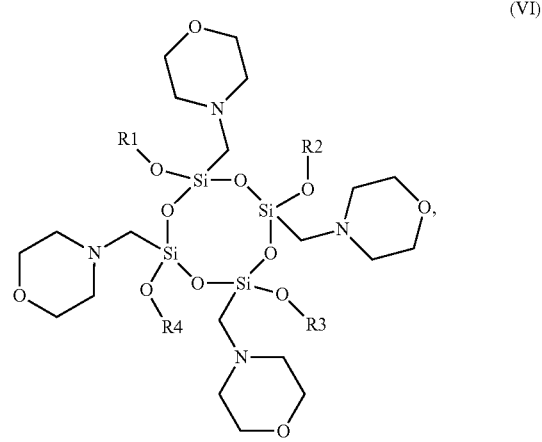

in which

R1, R2, R3, and R4 mutually independently denote —H, —CH₃, a group D, a structural unit (I), (II), or (III), or an oligomeric or polymeric residue including structural units of formulas (I), (II), or (III), or two of the residues R1, R2, R3, and R4 denote a structural unit —Si(R6)(R5)-, where R5=—CH₃ or a structural unit of formula (I) or (II) or (III) or an oligomeric or polymeric residue including structural units of formulas (I), (II), or (III), R6=—OH, —CH₃, or a structural unit of formula (I) or (II) or (III) or an oligomeric or polymeric residue including structural units of formulas (I), (II), or (III).

In preferred silicones of formula (VI), at least one of the residues R1, R2, R3, or R4 denotes an oligomeric or polymeric residue including structural units of formulas (I), (II), or (III).

In further preferred silicones of formula (VI), at least one of the residues R1, R2, R3, or R4 denotes an oligomeric or polymeric residue including structural units of formulas (I) and (II).

In even further preferred silicones of formula (VI), at least one of the residues R1, R2, R3, or R4 denotes an oligomeric or polymeric residue including structural units of formulas (I) and (II) and (III).

At least one of the residues R1, R2, R3, or R4 preferably denotes an —[—Si(CH₃)₂—O]$_m$ grouping, i.e. an oligomer or polymer of structural unit (I). In addition, structural unit (II) or an oligomer or polymer thereof preferably is never bound in the molecule alone, but instead always in a statistical distribution with further structural units of formula (I) as one of the residues R1, R2, R3, or R4.

Preferred silicones of formula (VI) can be described by formula (VI a)

in which

R1, R2, and R4 mutually independently denote —H, —CH₃, a group D, a structural unit (I), (II), or (III), or an oligomeric or polymeric residue including structural units of formulas (I), (II), or (III), or two of the residues R1, R2, and R4 denote a structural unit —Si(R6)(R5)-, where R5=—CH₃ or a structural unit of formula (I) or (II) or (III) or an oligomeric or polymeric residue including structural units of formulas (I), (II), or (III), R6=—OH, —CH₃, or a structural unit of formula (I) or (II) or (III) or an oligomeric or polymeric residue including structural units of formulas (I), (II), or (III), A denotes a structural unit (I), (II), or (III) bound via —O—, or an oligomeric or polymeric residue bound via —O— including structural units of formulas (I), (II), or (III), or half of an oxygen atom connecting to a structural unit (III), or denotes —OH, D denotes an —H, —Si(CH₃)₃, —Si(CH₃)₂OH, —Si(CH₃)₂OCH₃ group, a, b, and c denote integers from 0 to 1000, with the provision that a+b+c>0, n, and o denote integers from 1 to 1000.

Further preferred silicones of formula (VI) can be described by formula (VI b)

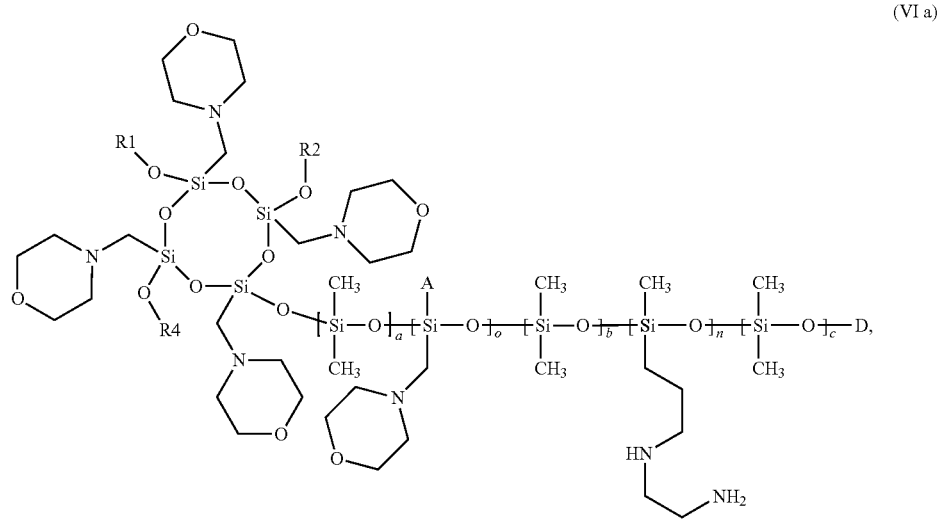

(VI a)

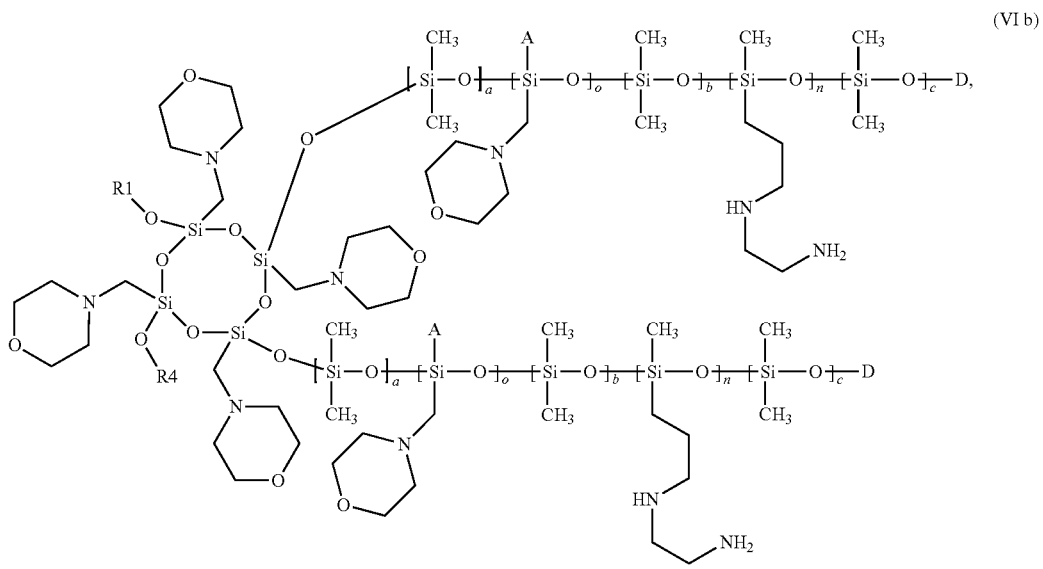

(VI b)

in which the residues and indices are as defined above.

Particularly preferred silicones of formula (VI) can be described by formula (VI c)

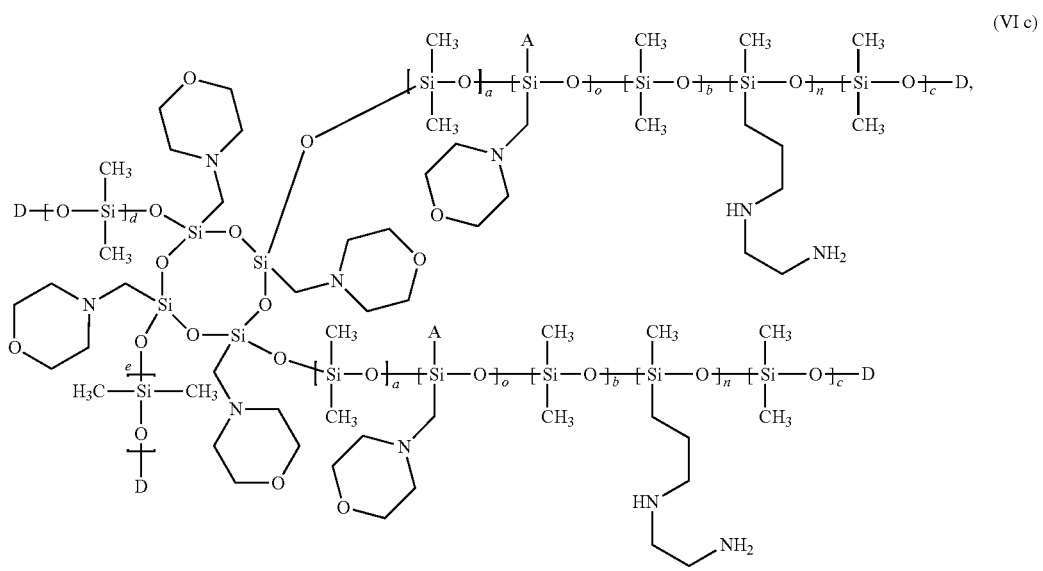

(VI c)

in which the residues and indices are as defined above, and the indices d and e denote integers between 0 and 1000.

In formulas (VI a), (VI b), and (VI c), at least one of the groupings D preferably denotes —Si(CH$_3$)$_2$OH.

The silsesquioxane structures can be even more pronounced in the 4-morpholinomethyl-substituted silicones used according to the present invention, which intensifies the advantageous effects. Particularly cosmetic agents according to the present invention are characterized in that they include at least one 4-morpholinomethyl-substituted silicone that comprises structural units of formula (VII)

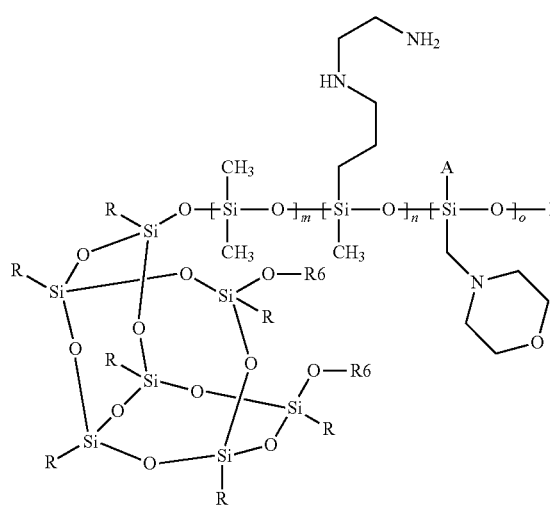

(VII)

in which

A denotes a structural unit (I), (II), or (III) bound via —O—, or an oligomeric or polymeric residue bound via —O— including structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, R denotes a 4-morpholinomethyl residue, R6 denotes —H or the grouping

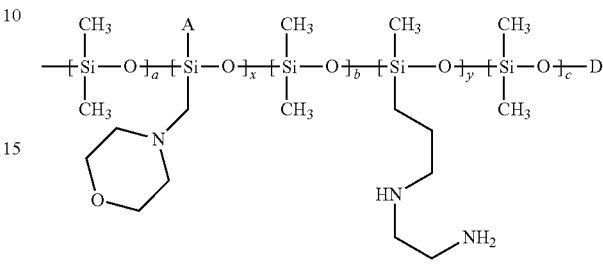

wherein the siloxane units m, n, and o and a, b, c, x, and y are present in statistically distributed fashion.

Particularly preferred cosmetic agents according to the present invention include at least one silicone of the following formula (VII a)

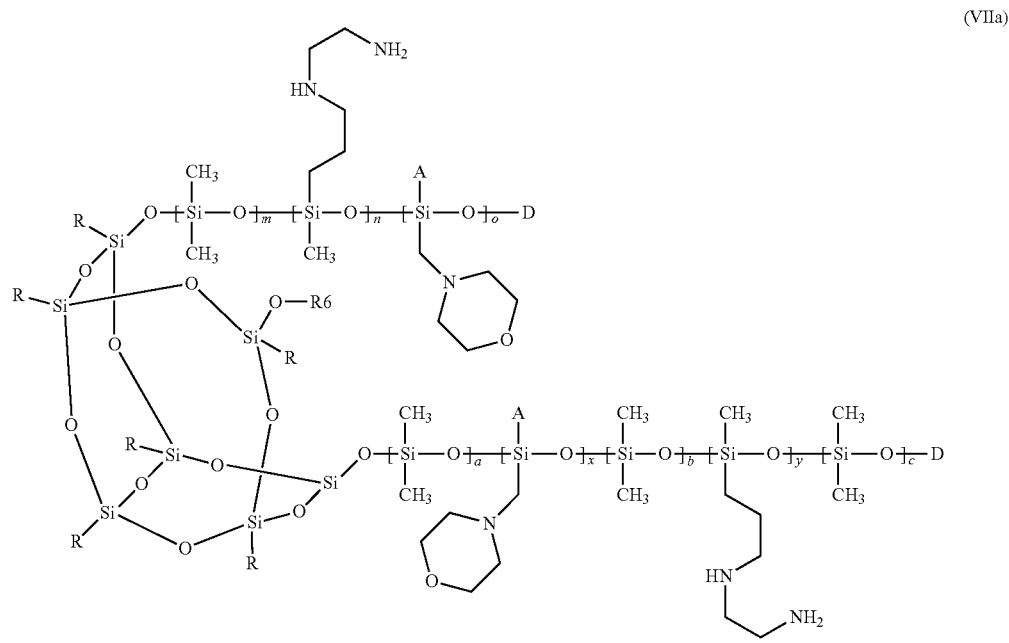

(VIIa)

with the definitions as for formula (VII).
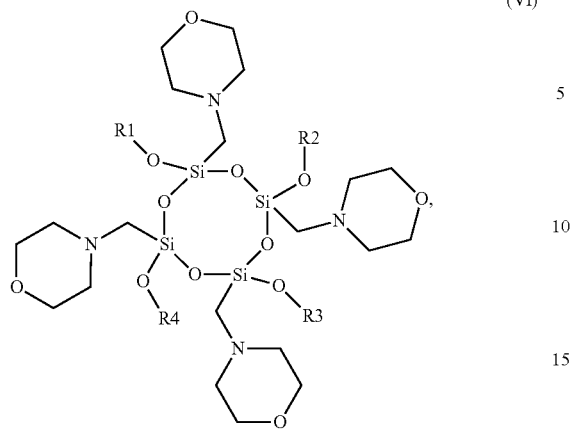
(VI)
Very particularly preferred cosmetic agents according to the present invention include at least one silicone of the following formula (VII b)
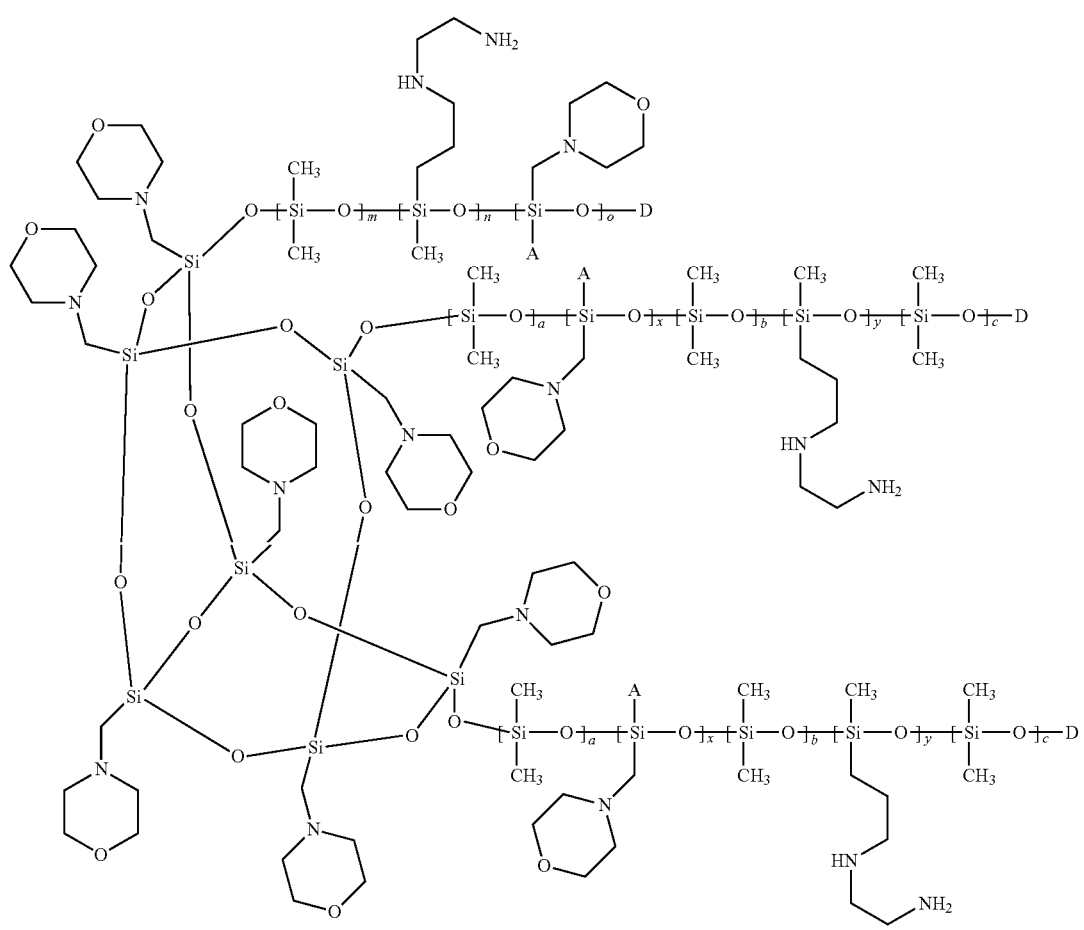
(VIIb)
with the definitions as for formula (VII).

In formulas (VII), (VII a), and (VII b), the bridging oxygen atoms between the morpholinomethyl-substituted silicon atoms can also be supplemented by an —[—Si(CH$_3$)$_2$—O]$_m$ grouping, i.e. an oligomer or polymer of structural unit (I). Corresponding hair treatment agents according to the present invention which include at least one 4-morpholinomethyl-substituted silicone that comprises structural units of formula (VIII)

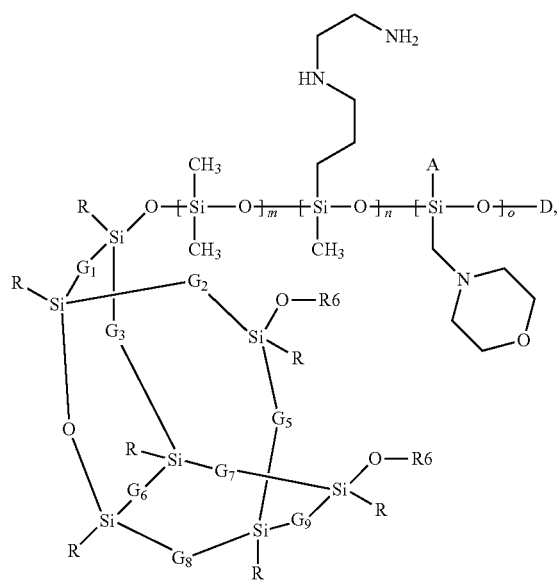

(VIII)

in which

A denotes a structural unit (I), (II), or (III) bound via —O—, or an oligomeric or polymeric residue bound via —O— including structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, G1 to G9 mutually independently denote —O— or an —[—Si(CH$_3$)$_2$—O]$_m$ group where m=1 to 200, R denotes a 4-morpholinomethyl residue, R6 denotes —H or the grouping

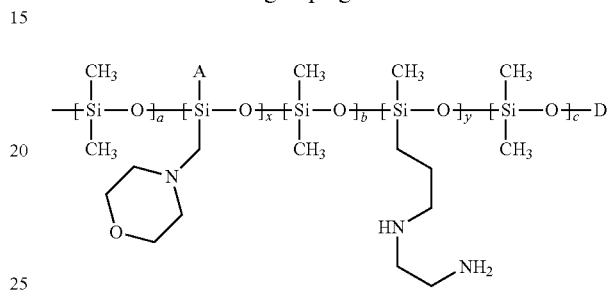

wherein the siloxane units m, n, and o, and a, b, c, x, and y, are present in statistically distributed fashion.

Particularly preferred cosmetic agents according to the present invention include at least one silicone of the following formula (VIII a)

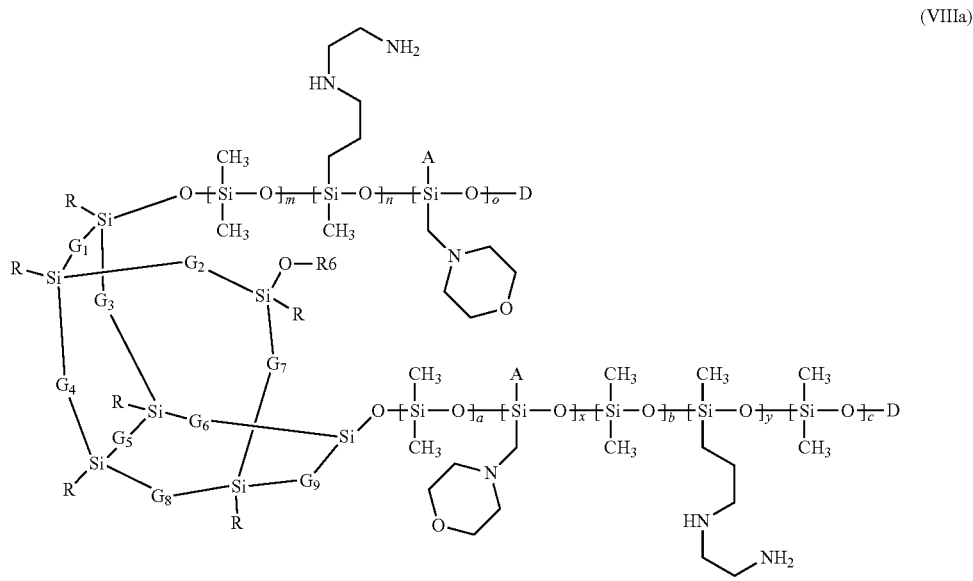

(VIIIa)

with the definitions as for formula (VIII).

Very particularly preferred cosmetic agents according to the present invention include at least one silicone of the following formula (VIII b)

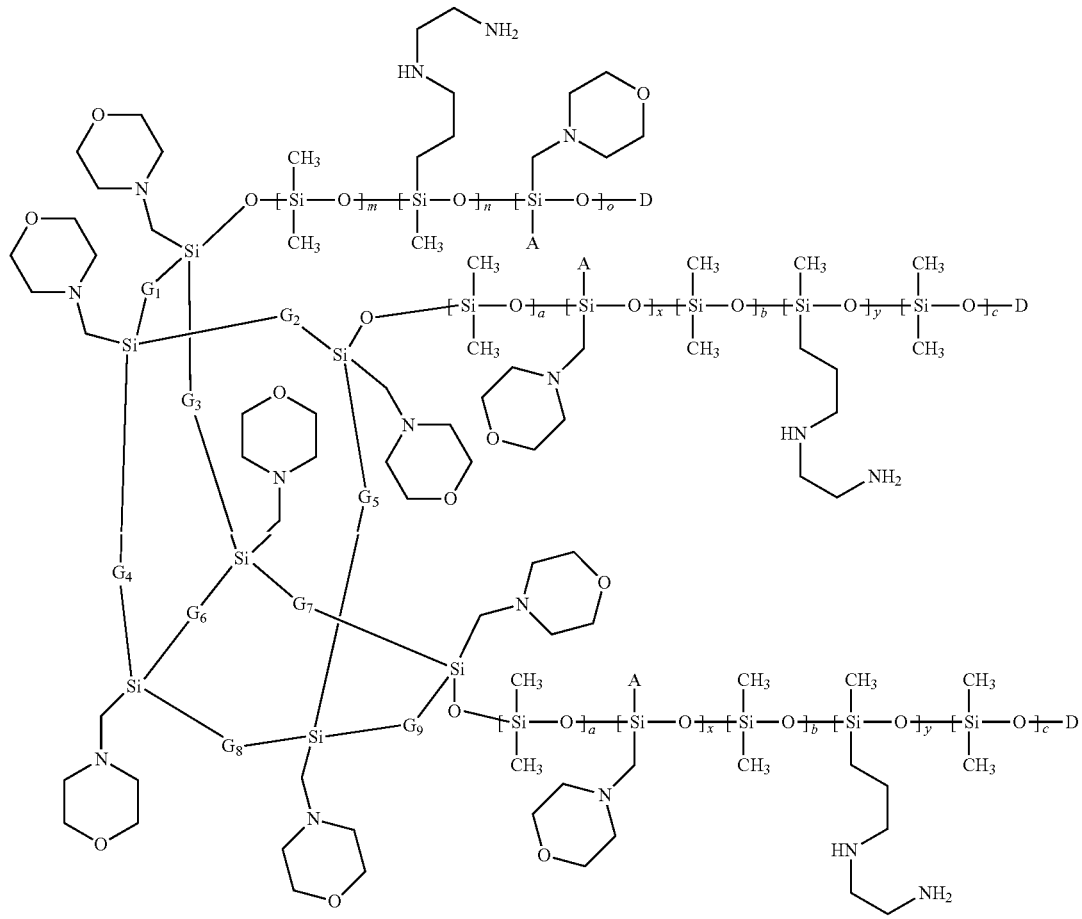

(VIIIb)

with the definitions as for formula (VIII).

Regardless of which special 4-morpholinomethyl-substituted silicone is included in the cosmetic agents according to the present invention, cosmetic agents according to the present invention that include a 4-morpholinomethyl-substituted silicone in which more than 50 mol % of the structural units are dimethylsiloxy units, i.e. in which structural unit (I) makes up at least half of all structural units of the silicone used, are preferred.

In other words, silicones in which m>(n+o) or (a+b+c)>(n+o) are preferred.

Even further preferred cosmetic agents include a 4-morpholinomethyl-substituted silicone in which more than 90 mol % of the structural units are dimethylsiloxy units, i.e. in which structural unit (I) makes up more than nine tenths of all structural units of the silicone used.

In other words, silicones in which m>10(n+o) or (a+b+c)>10(n+o) are preferred.

Even further preferred cosmetic agents include a 4-morpholinomethyl-substituted silicone in which more than 98 mol % of the structural units are dimethylsiloxy units, i.e. in which structural unit (I) makes up at least ninety-eight hundredths of all structural units of the silicone used.

In other words, silicones in which m>50(n+o) or (a+b+c)>50(n+o) are preferred.

Even further preferred cosmetic agents include a 4-morpholinomethyl-substituted silicone in which more than 98.5 mol % of the structural units are dimethylsiloxy units, i.e. in which structural unit (I) makes up at least nine hundred eighty-five thousandths of all structural units of the silicone used.

In other words, silicones in which m>75(n+o) or (a+b+c)>75(n+o) are preferred.

Even further preferred cosmetic agents include a 4-morpholinomethyl-substituted silicone in which more than 99 mol % of the structural units are dimethylsiloxy units, i.e. in which structural unit (I) makes up at least ninety-nine hundredths of all structural units of the silicone used.

In other words, silicones in which m>100(n+o) or (a+b+c)>100(n+o) are preferred.

In summary, preferred cosmetic agents according to the present invention are characterized in that they include at least one 4-morpholinomethyl-substituted silicone in which
m>(n+o) or (a+b+c)>(n+o), preferably
m>10(n+o) or (a+b+c)>10(n+o), particularly preferably
m>50(n+o) or (a+b+c)>50(n+o), more preferably
m>75(n+o) or (a+b+c)>75(n+o), and in particular
m>100(n+o) or (a+b+c)>100(n+o).

The 4-morpholinomethyl-substituted silicone(s) can be employed in varying quantities depending on the intended use of the agents according to the present invention. Preferred cosmetic agents according to the present invention are characterized in that they include, based on their weight, 0.00001 to 10 wt %, preferably 0.0001 to 7.5 wt %, particularly preferably 0.001 to 5 wt %, more preferably 0.01 to 3 wt %, and in particular 0.1 to 1 wt % 4-morpholinomethyl-substituted silicone(s).

It has become apparent that the effect of the silicones employed according to the present invention can be further increased if specific nonionic components are likewise included in the agents according to the present invention. These nonionic components furthermore have positive effects on the shelf stability of the agents according to the present invention. Nonionic components that are particularly suitable here are ethoxylates of decanol, undecanol, dodecanol, tridecanol, etc. Ethoxylated tridecanols have proven to be particularly suitable, and are incorporated with particular preference into the agents according to the present invention. Cosmetic compositions particularly preferred according to the present invention include, based on their weight, 0.00001 to 5 wt %, preferably 0.0001 to 3.5 wt %, particularly preferably 0.001 to 2 wt %, more preferably 0.01 to 1 wt %, and in particular 0.1 to 0.5 wt % branched ethoxylated tridecanol (INCI name: Trideceth-5) or α-isotridecyl-ω-hydroxypolyglycol ether (INCI name: Trideceth-10), or mixtures thereof.

Morpholinomethyl-substituted silicone(s) preferred according to the present invention comprise both hydroxy groups and alkoxy groups. Cosmetic compositions particularly preferred according to the present invention include hydroxy-terminated 4-morpholinomethyl-substituted silicone(s) in which the molar ratio of hydroxy to alkoxy is in the range from 0.2:1 to 0.4:1, preferably in the range from 1:0.8 to 1:1.1.

The average molecular weight of the silicone is preferably from 2000 to 200,000, and even more preferably from 5000 to 100,000, in particular 10,000 to 50,000 dalton. Cosmetic compositions in which the weight-average molar mass of the 4-morpholinomethyl-substituted silicone of formula (V) included therein is in the range from 2000 to 1,000,000 gmol$^{-1}$, preferably in the range from 5000 to 200,000 gmol$^{-1}$, are preferred.

The average molecular weights of aminosubstituted silicones are measurable, for example, by gel permeation chromatography (GPC) at room temperature in polystyrene. Styragel μ columns can be selected as columns, THF as an eluent, and 1 ml/min as a flow rate. Detection is accomplished preferably by refractometry using a UV meter.

The 4-morpholinomethyl-substituted silicone(s) of formula (V) are used preferably as an oil-in-water emulsion. The oil-in-water emulsion can include one or more surfactants. The surfactants can be of any kind, preferably cationic and/or nonionic. The number-average average size of the silicone droplets in the emulsion is preferably between 3 nm and 500 nm, particularly preferably between 5 nm and 60 nm (inclusive), and in particular between 10 nm and 50 nm (inclusive).

Cosmetic compositions according to the present invention in which the 4-morpholinomethyl-substituted silicone of formula (V) is present in the form of an oil-in-water emulsion in which the number-average size of the silicone particles in the emulsion is in the range from 3 to 500 nm, preferably in the range from 5 to 60 nm, are preferred according to the present invention.

The 4-morpholinomethyl-substituted silicones of formula (V) are preferably selected so that the contact angle of human hair with water, after treatment with a composition that includes 2% (active agent) of the aforesaid silicone, is between 90° and 180° (inclusive), preferably between 90 and 130° (inclusive).

A further essential constituent of the compositions according to the present invention is a thickening agent, whose function is to increase the viscosity of the composition.

In cosmetic compositions preferred according to the present invention, the thickening agents are selected from among:
  (i.) associative thickening agents;
  (ii.) crosslinked homopolymers of acrylic acid;
  (iii.) crosslinked copolymers of (meth)acrylic acid and alkyl ($C_{1-6}$) acrylate;
  (iv.) nonionic homopolymers and copolymers that include monomers having an ethylenically unsaturated bond of the ester type and/or amide type;
  (v.) homopolymers of ammonium acrylate or copolymers of ammonium acrylate and acrylamide;
  (vi.) polysaccharides;
  (vii.) fatty alcohols with $C_{12-30}$;
  (viii.) fatty acid amides.

"Associative thickening agents" according to the invention are thickening agents having both hydrophilic and hydrophobic units, in particular having at least one $C_8$ to $C_{30}$ fat chain and at least one hydrophilic unit.

Cosmetic compositions preferred according to the present invention include as an associative thickening agent an associative polymer that is selected from
  (i.) nonionic amphiphilic polymers that include at least one fat chain and at least one hydrophilic unit;
  (ii.) anionic amphiphilic polymers that include at least one hydrophilic unit and at least one unit having a fat chain;
  (iii.) cationic amphiphilic polymers that include at least one hydrophilic unit and at least one unit having a fat chain;
  (iv.) amphoteric amphiphilic polymers that include at least one hydrophilic unit and at least one unit having a fat chain,
wherein the fat chains comprise 10 to 30 carbon atoms.

The nonionic amphiphilic polymer having at least one fatty acid chain and at least one hydrophilic unit is preferably selected from
(1) celluloses that are modified with groups that comprise at least one fat chain;
(2) hydroxypropyl guar compounds that are modified with groups that comprise at least one fat chain;
(3) urethane polyethers that include at least one fat chain, such as alkyl groups or alkenyl groups having 10 to 30 carbon atoms;
(4) copolymers of vinylpyrrolidone and hydrophobic monomers having a fat chain;
(5) copolymers of alkyl ($C_{1-6}$) methacrylates or alkyl ($C_{1-6}$) acrylates and amphiphilic monomers that include at least one fat chain;
(6) copolymers of hydrophilic methacrylates or acrylates and hydrophobic monomers that include at least one fat chain.

Examples of (1) are hydroxyethyl celluloses having groups that include at least one fat chain, such as alkyl, arylalkyl, alkylaryl, or mixtures thereof, wherein the alkyl groups are preferably selected from $C_8$ to $C_{22}$, such as the product Natrosol Plus Grade 330 CS (C16 alkyl) of the Aqualon company, or the product Bermocoll EHM 100 of the Berol Nobel company, or alkylphenols equipped with polyalkylene glycol ether groups, such as the product AMERCELL POLYMER HM-1500 (polyethylene glycol (15) nonylphenol ether sulfate) of Amerchol.

Examples of (2) are the product Esaflor HM 22 (C22 alkyl chain) of the Lamberti company, MiraCare XC95-3 (C14 alkyl chain), and RE205-1 (C20 alkyl chain) of Rhodia Chimie.

Examples of (3) are the products Dapral T 210 and T 212 Dapral of Akzo, or the products Aculyn 44 und 46 of Rohm & Haas.

Examples of (4) are Antaron V216 or V216 GANEX (vinylpyrrolidone/hexadecene copolymer) of ISP, and Antaron V220 or V220 GANEX (vinylpyrrolidone/eicosene) of ISP.

An example of (5) is the oxyethylenated copolymer of methyl methacrylate/stearyl acrylate that is marketed by Goldschmidt under the name Antil 208.

An example of (6) is the copolymer of polyethylene glycol methacrylate and lauryl methacrylate.

Cosmetic compositions preferred according to the present invention are therefore characterized in that the nonionic amphiphilic polymers that include at least one fatty acid chain and at least one hydrophilic unit are selected from (1) celluloses that are modified with groups that comprise at least one fat chain;
(2) hydroxypropyl guar compounds that are modified with groups that comprise at least one fat chain;
(3) urethane polyethers that include at least one fat chain, such as alkyl groups or alkenyl groups having 10 to 30 carbon atoms;
(4) copolymers of vinylpyrrolidone and hydrophobic monomers having a fat chain;
(5) copolymers of alkyl ($C_{1-6}$) methacrylates or alkyl ($C_{1-6}$) acrylates and amphiphilic monomers that include at least one fat chain;
(6) copolymers of hydrophilic methacrylates or acrylates and hydrophobic monomers that include at least one fat chain.

Among the anionic amphiphilic polymers of the invention having at least one hydrophilic and at least one fat chain, those having at least one allyl ether unit having a fat chain and at least one hydrophilic unit made up of an ethylenically unsaturated anionic monomer, in particular acrylic acid, methacrylic acid, or mixtures thereof, are preferred.

Allyl ethers having a fat chain corresponding to the monomer of the formula (M-III)

$$CH_2=C(R1)CH_2-OB_nR \qquad (M\text{-}III),$$

wherein R1 is —H or —$CH_3$, B identifies an ethylene oxide grouping, n signifies zero or an integer between 1 and 100, R represents a hydrocarbon residue selected from alkyl, arylalkyl, aryl, alkylaryl, cycloalkyl having 10 to 30 carbon atoms, preferably 10 to 24, and even more chiefly 12 to 18 carbon atoms, are preferred.

Particularly preferred units of formula (M-III) are those in which R1=—H, n=10, and R is a stearyl residue (C18).

Among these anionic amphiphilic polymers, acrylates having 20 to 60 wt % acrylic acid and/or methacrylic acid, 5 to 60 wt % low-alkyl (meth)acrylates, from 2 to 50 wt % allyl ether having a fat chain of formula (M-III), and 0 to 1 wt % crosslinker, are particularly preferred.

A copolymer of diallyl phthalate, (meth)acrylate, allyldivinylbenzene dimethacrylate, (poly)ethylene glycol, and methylene bisacrylamide is, for example, commercially usual.

Particularly preferred terpolymers of methacrylic acid, ethyl acrylate, polyethylene glycol (10 EO) stearyl alcohol ether (Steareth-10) are sold under the names SALCARE SC 80 and SALCARE SC90; these are 30% aqueous emulsions of a crosslinked terpolymer of methacrylic acid, ethyl acrylate, and steareth-10 allyl ether (40/50/10).

Preferred cosmetic compositions according to the present invention are characterized in that the anionic amphiphilic polymers that include at least one hydrophilic unit and at least one unit having a fat chain are selected from the compounds that include at least one allyl ether unit having a fat chain and at least one hydrophilic unit that is constructed from an ethylenically unsaturated anionic monomer, compounds that include at least one hydrophilic unit of the type of an olefinically unsaturated carboxylic acid and at least one hydrophobic unit exclusively of the type of an alkyl ($C_{1-30}$) ester of an unsaturated carboxylic acid, and methacrylic acid/methacrylate/dimethyl meta-isopropenylbenzyl isocyanate copolymers of an ethoxylated alcohol.

The anionic amphiphilic polymers can further be selected from those which include at least one hydrophilic unit of olefinically unsaturated carboxylic acids and at least one hydrophobic unit of the type of ($C_{10}$ to $C_{30}$) alkyl esters of an unsaturated carboxylic acid.

The hydrophilic unit of the olefinically unsaturated carboxylic acid type corresponds, for example, to the monomer of formula (M-IV):

$$H_2C=(C(R1)C(O)-OH \qquad (M\text{-}IV)$$

in which R1 is selected from —H, —$CH_3$, and —$C_2H_5$, i.e. acrylic-acid, methacrylic-acid, and ethacrylic-acid units. And the hydrophobic unit of the type of ($C_{10}$ to $C_{30}$) esters of an unsaturated carboxylic acid corresponds, for example, to the monomer of formula (V):

$$H_2C=C(R1)C(O)-OR2 \qquad (M\text{-}V)$$

in which R1 is selected from —H, —$CH_3$, and $C_2H_5$ (i.e. acrylate, methacrylate, and ethacrylate units), R2 is selected from $C_{10}$ to $C_{30}$ alkyl residues, for example a $C_{12}$ to $C_{22}$ alkyl residue.

Examples of ($C_{10}$ to $C_{30}$) alkyl esters of unsaturated carboxylic acids are lauryl acrylate, stearyl acrylate, decyl acrylate, isodecyl acrylate, and dodecyl acrylate, and the corresponding methacrylates lauryl methacrylate, stearyl methacrylate, decyl methacrylate, isodecyl methacrylate, and dodecyl methacrylate.

Representative anionic amphiphilic polymers that can be used are also polymers of a mixtures of monomers comprising (i) acrylic acid esters of formula (M-VI)

$$H_2C=C(R1)C(O)-OR2 \qquad (M\text{-}VI)$$

in which R1 is selected from —H, —$CH_3$ (i.e. acrylate, methacrylate units, R2 is selected from $C_{10}$ to $C_{30}$ alkyl residues, for example a $C_{12}$ to $C_{22}$ alkyl residue, and a crosslinking agent; such as polymers of 95% to 60 wt % acrylic acid (hydrophilic unit), 4% to 40 wt % C10 to C30 alkyl acrylate (hydrophobic unit), and 0% to 6 wt % crosslinking of polymerizable monomers, or polymers derived from 98% to 96% of the weight of acrylic acid (hydrophilic unit), 1% to 4 wt % C10 to C30 alkyl acrylate (hydrophobic unit), and 0.1% to 0.6 wt % crosslinking of polymerizable monomers, or (ii) acrylic acid and lauryl methacrylate, such as the polymers that are constituted from 66 wt % acrylic acid and 34 wt % lauryl methacrylate.

The crosslinking agent can be a monomer that includes a group having at least one other polymerizable group whose unsaturated bonds are not conjugated with one another. Polyallyl ethers, for example, such as polyallylsucrose and polyallylpentaerythritol, may be recited.

Preferred among the polymers mentioned above are, for example, the products of the Goodrich company under the commercial names Pemulen TR1, Pemulen TR2, Carbopol 1382, and others, for example Pemulen TR1, and the Coatex SX product of Seppic.

Also to be recited among anionic amphiphilic fatty-acid-chain polymers are the methacrylic acid/methyl acrylate/ethoxylated alkyldimethyl-meta-isopropenylbenzyl isocyanate copolymers that are marketed under the name Viscophobe DB 1000 by the Amerchol company.

Cationic amphiphilic polymers can also be used, for example those of quaternized cellulose derivatives and polyacrylates having amino side groups.

The quaternized cellulose derivatives are constituted, for example, from selected quaternized celluloses having groups that include at least one fat chain, such as alkyl, arylalkyl, and alkylaryl groups having at least 8 carbon atoms, and mixtures thereof. Quaternized hydroxyethyl celluloses having groups that include at least one fat chain, such as alkyl, arylalkyl, and alkylaryl groups having at least 8 carbon atoms, and mixtures thereof, are preferred. Quaternized and non-quaternized polyacrylates having amino side groups and, for example, hydrophobic groups, such as Steareth 20 (polyoxyethylenated (20) stearyl alcohol) and (C10-C30)-Alkyl PEG-20 Itaconate, are likewise preferred.

The alkyl residues of the quaternized celluloses and hydroxyethyl celluloses recited above include, for example, 8 to 30 carbon atoms. The aryl residues are selected, for example, from phenyl, benzyl, naphthyl, and anthryl groups. Examples of quaternized alkylhydroxyethyl celluloses made up of C8 to C30 fatty acid chains are the products Quatrisoft LM 200, LM-X Quatrisoft 529-18-A, Quatrisoft LM-X 529-18B (C12 alkyl), and Quatrisoft LM-X 529-8 (C18) sold by the Amerchol company, and the products Crodacel QM, Crodacel QL (C12 alkyl), and Crodacel QS (C18) of the Croda company.

Examples of polyacrylates having amino side chains are the polymers 8781-124B or 9492-103 and Structure Plus of the National Starch company.

To be recited among amphoteric amphiphilic polymers having at least one hydrophilic unit and at least one fatty-acid-chain unit are, for example, methacrylamidopropyltrimethyl ammonium/acrylic acid/C10 to C20 alkyl methacrylate copolymers, wherein the alkyl residue is, for example, a stearyl residue.

The associative thickening agents in the cosmetic compositions can be employed, for example, in solution or in dispersion, having a concentration of 1% active material in water and having a viscosity, measured with a Rheomat RM 180 rheometer at 25° C., that is greater than 0.1 cps and preferably greater than 0.2 cps at a shear rate of 200 s$^{-1}$.

In summary, preferred cosmetic compositions according to the present invention are characterized in that the cationic amphiphilic polymers are selected from quaternized cellulose derivatives, and from polyacrylates having aminated side chains.

Further preferred cosmetic compositions are characterized in that the amphoteric amphiphilic polymers that include at least one side chain are selected from copolymers of methacrylamidopropyltrimethylammonium chloride/alkyl (C$_{10-30}$) methacrylate.

(ii) Among the crosslinked acrylic acid homopolymers that can be mentioned are those having an allyl alcohol ether of the sugar series, such as the products sold by the Goodrich company under the name Carbopol 980, 981, 954, 2984, and 5984, or the products of the 3 VSA company under the names Synthalen M and Synthalen K.

(iii) Crosslinked copolymerizates of (meth)acrylic acid and C1 to C6 alkyl acrylates can be selected from crosslinked copolymers of methacrylic acid and ethyl acrylate in the form of an aqueous dispersion that includes 38% active material.

These are sold under the names Viscoatex 538C by the Coatex company. Crosslinked copolymers of acrylic acid and ethyl acrylate in the form of an aqueous dispersion that includes 28% active material are marketed under the name Aculyn 33 by the Rohm & Haas company. Crosslinked copolymers of methacrylic acid and ethyl acrylate comprising an aqueous dispersion having 30% active material are manufactured and sold by the Noveon company under the name Carbopol Aqua SF-1.

(iv) The following may be recited among the nonionic homo- or copolymers of ethylenically unsaturated monomers of the ester type and/or amide type: Cyanamer P250 of the Cytec company (polyacrylamide); PMMA MBX-8C of the US Cosmetics company (methyl methacrylate/ethylene glycol dimethacrylate copolymer); Acryloid B66 of the Rohm & Haas company (butyl methacrylate/methyl methacrylate copolymer); BPA 5000 of the Kobo company (polymethyl methacrylate).

(v) Ammonium acrylate homopolymers that can be mentioned are the product Microsap PAS 5193 of the Hoechst company.

Copolymers of ammonium acrylate and of acrylamide are marketed by the Hoechst company as a product under the name Bozepol C Nouveau or Product PAS 5193.

(vi) The polysaccharides are selected, for example, from glucans, modified and unmodified starches (derived, for example, from cereals, for example wheat, corn, or rice, from vegetables, for example yellow peas, and tubers, for example potatoes or cassava), amylose, amylopectin, glycogen, dextrans, cellulose and derivatives thereof (methyl celluloses, hydroxyalkyl celluloses, ethylhydroxyethyl celluloses, and carboxymethyl celluloses), mannans, xylans, lignins, arabans, galactans, galacturonans, chitin, chitosan, glucuronoxylans, arabinoxylans, xyloglucans, glucomannans, pectic acids and pectins, alginic acid and alginates, arabinogalactans, carrageenans, agar, glycosaminoglucans, gum arabics, tragacanths, ghatti seed flour, karaya seed flour, locust bean flour, galactomannans, such as guar gum and nonionic derivatives (hydroxypropyl guar), and xanthan gum, and mixtures thereof.

Included among the starches that can be used are, for example, macromolecules in the form of polymers that comprise elementary units (anhydroglucose units). The number of these units, and their connections, make it possible to distinguish between amylose (linear polymer) and amylopectin (branched polymers). The relative proportions of amylose and amylopectin, and also the degree of polymerization, can vary as a function of the botanical origin of the starch.

The botanical origin of the starch molecules can be cereals or tubers. The starches can thus be selected, for example, from corn starch, rice starch, cassava, tapioca, barley, potato, wheat, sorghum starch, and pea starch.

Starches are as a rule in the form of a white powder that is insoluble in cold water and has an elementary particle size in the range from 3 to 100 micrometers. Starches can optionally be C1-C6 hydroxyalkylated or C1-C6 acylated (e.g. acetylated). Starches can also be subjected to heat treatments. Distarch phosphates or compounds that are rich in distarch phosphates, for example the products under the references Prejel VA-70-T AGGL (gelatinized hydroxypropylated cassava distarch phosphate) or Prejel TK1 (gelatinized cassava distarch phosphate) or Prejel 200 (gelatinized acetylated cassava distarch phosphate) of the Avebe company, or Structure ZEA of National Starch (hydroxypropylated corn distarch phosphate), can likewise be used.

The guar gums can be modified or unmodified. Unmodified guar gums are, for example, the products Vidogum GH 175 of the Unipectine company, and Meyro-Guar 50 and Jaguar C of the Meyhall company. Modified nonionic guar gums are, for example, modified with C1 to C6 hydroxyalkyl groups. Hydroxyalkyl groups can be, for example, hydroxymethyl, hydroxyethyl, hydroxypropyl, and hydroxybutyl groups.

In summary, cosmetic compositions according to the present invention in which the polysaccharides are selected from glucans, modified or unmodified starch compounds, amylose, amylopectin, glycogen, dextrans, celluloses and derivatives thereof, mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenins, agar-agar, glycosaminoglucans, gum arabic, tragacanth, ghatti gum, karaya gum, locust bean flour, galactomannans, xanthan gum, and mixtures thereof, are preferred.

Nonionic guar gums of this kind, optionally substituted with hydroxyalkyl groups, are marketed for example under the commercial name Jaguar HP8, Jaguar HP60, and Jaguar HP120, Jaguar DC 293, and Jaguar HP 105 by the Rhodia Chimie (Meyhall) company, or under the name Galactasol 4H 4FD2 by the Aqualon company.

Among the celluloses, hydroxyethyl cellulose and hydroxypropyl celluloses, for example, can be used. The products Klucel EF, Klucel H, Klucel LHF, Klucel MF, and Klucel G of the Aqualon company may be mentioned.

(vii) Fatty alcohols are selected, for example, from myristyl alcohol, cetyl alcohol, stearyl alcohol, and behenyl alcohol.

Cosmetic compositions preferred according to the present invention include the thickening agent or agents in a total quantity from 0.001 to 20 wt %, preferably from 0.01 to 15 wt %, more preferably from 0.1 to 10 wt %, and in particular from 0.25 to 5 wt %, based on the total weight of the composition.

Depending on the intended use, the agents according to the present invention include further essential ingredients. Cleaning or care-providing compositions, for example shampoos or conditioners, include at least one surfactant, wherein surface-active substances are referred to as "surfactants" or as "emulsifier agents" depending on the area of use, and are selected from anionic, cationic, zwitterionic, ampholytic, and nonionic surfactants and emulsifier agents.

Cosmetic agents preferred according to the present invention are characterized in that they include, based on their weight, 0.5 to 70 wt %, preferably 1 to 60 wt %, and in particular 5 to 25 wt % anionic and/or nonionic and/or cationic and/or amphoteric surfactant(s). Surfactants from the aforementioned groups to be used particularly preferably according to the present invention are disclosed in detail on pages 26 to 37 of the priority document.

The care-providing effects of the agents according to the present invention can be even further intensified by employing specific care-providing substances. The latter are preferably selected from specific groups of care-providing substances known per se, since these care-providing substances harmonize outstandingly with the 4-morpholinomethyl-substituted silicones used according to the present invention in terms of formulation engineering and care-providing effect.

Cosmetic agents preferred according to the present invention are characterized in that they additionally include, based on their weight, care-providing substances in quantities from 0.001 to 10 wt %, preferably 0.005 to 7.5 wt %, particularly preferably 0.01 to 5 wt %, and in particular 0.05 to 2.5 wt %, wherein preferred care-providing substance(s) are selected from the group:

i. L-carnitine and/or salts thereof;
ii. panthenol and/or pantothenic acid;
iii. 2-furanone and/or derivatives thereof, in particular pantolactone;
iv. taurine and/or salts thereof;
v. niacinamide;
vi. ubiquinone;
vii. ectoin;
viii. allantoin.

In hair treatment agents according to the present invention of this embodiment, the 4-morpholinomethyl-substituted silicones are combined with at least one care-providing substance that is selected from L-carnitine and/or salts thereof, panthenol and/or pantothenic acid, 2-furanone and/or derivatives thereof, in particular pantolactone, taurine and/or salts thereof, niacinamide, ubiquinones, ectoin, allantoin. These care-providing substances are described below.

L-Carnitine (IUPAC name (R)-(3-carboxy-2-hydroxypropyl)-N,N,N-trimethylammonium hydroxide) is a naturally occurring vitamin-like substance. As a betaine, L-carnitine can form addition compounds and double salts. L-Carnitine derivatives preferred according to the present invention are selected in particular from acetyl-L-carnitine, L-carnitine fumarate, L-carnitine citrate, lauroyl-L-carnitine, and particularly preferably L-carnitine tartrate. The aforesaid L-carnitine compounds are obtainable, for example, from Lonza GmbH (Wuppertal, Germany).

Preferred cosmetic agents according to the present invention are characterized in that they include, based on their weight, 0.001 to 10 wt %, preferably 0.005 to 7.5 wt %, particularly preferably 0.01 to 5 wt %, and in particular 0.05 to 2.5 wt % L-carnitine or L-carnitine derivatives, wherein preferred L-carnitine derivatives are selected from acetyl-L-carnitine, L-carnitine fumarate, L-carnitine citrate, lauroyl-L-carnitine, and in particular L-carnitine tartrate.

Panthenol (IUPAC-Name: (+)-(R)-2,4-dihydroxy-N-(3-hydroxypropyl)-3,3-dimethylbutyramide) is converted in the body to pantothenic acid. Pantothenic acid is a vitamin from the group of the B vitamins (vitamin B5).

Preferred cosmetic agents according to the present invention are characterized in that they include, based on its weight, 0.01 to 5 wt %, preferably 0.05 to 2.5 wt %, particularly preferably 0.1 to 1.5 wt %, and in particular 0.25 to 1 wt % panthenol ((+)-2,4-dihydroxy-N-(3-hydroxypropyl)-3,3-dimethylbutyramide).

Cosmetic agents preferred according to the present invention include, based on their weight, 0.01 to 15 wt %, preferably 0.025 to 12.5 wt %, particularly preferably 0.05 to 10 wt %, more preferably 0.1 to 7.5 wt %, and in particular 0.5 to 5 wt % of at least one 2-furanone derivative of formula (Fur-I) and/or of formula (Fur-II)

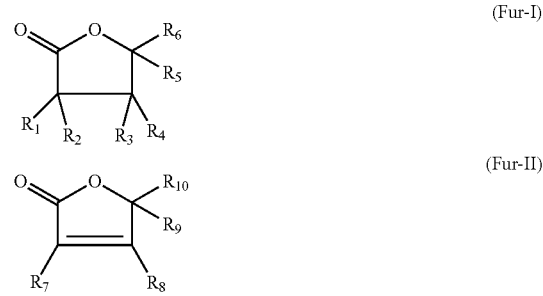

in which the residues $R^1$ to $R^{10}$ mutually independently denote:
- hydrogen, —OH, a methyl, methoxy, aminomethyl, or hydroxymethyl residue,
- a $C_2$ to $C_4$ saturated or mono- or diunsaturated, branched or linear hydrocarbon residue,
- a $C_2$ to $C_4$ saturated or mono- or diunsaturated, branched or linear mono-, di- or trihydroxy hydrocarbon residue,
- a $C_2$ to $C_4$ saturated or mono- or diunsaturated, branched or linear mono-, di- or triamino hydrocarbon residue,
- an —$OR^{11}$ group, having $R^{11}$ as a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue,
- an —$NR^{12}R^{13}$ group, wherein $R^{12}$ and $R^{13}$ each mutually independently denote hydrogen, a methyl residue, a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue,
- a —$COOR^{14}$ group, wherein $R^{14}$ denotes hydrogen, a methyl residue, a $C_2$ to $C_4$ saturated or mono- or diunsaturated, branched or linear hydrocarbon residue, a $C_2$ to $C_4$ saturated, mono- or diunsaturated, branched or linear mono-, di- or trihydroxy hydrocarbon residue, a $C_2$ to $C_4$ saturated or mono- or diunsaturated, branched or linear mono-, di- or triamino hydrocarbon residue,
- a —$CONR^{15}R^{16}$ group, wherein $R^{15}$ and $R^{16}$ each denote hydrogen, methyl, a $C_2$ to $C_4$ saturated or mono- or diunsaturated, branched or linear hydrocarbon residue, a $C_2$ to $C_4$ saturated, mono- or diunsaturated, branched or linear mono-, di- or trihydroxy hydrocarbon residue, a $C_2$ to $C_4$ saturated or mono- or diunsaturated, branched or linear mono-, di- or triamino hydrocarbon residue,
- a —$COR^{16}$ group, wherein $R^{16}$ denotes a methyl residue, a $C_2$ to $C_4$ saturated or mono- or diunsaturated, branched or linear hydrocarbon residue, a $C_2$ to $C_4$ saturated or mono- or diunsaturated, branched or linear mono-, di- or trihydroxy hydrocarbon residue, a $C_2$ to $C_4$ saturated or mono- or diunsaturated, branched or linear mono-, di- or triamino hydrocarbon residue,
- an —$OCOR^{17}$ group, wherein $R^{17}$ denotes a methyl residue, a $C_2$ to $C_{30}$ saturated or mono- or polyunsaturated, branched or linear hydrocarbon residue, a $C_2$ to $C_{30}$ saturated or mono- or polyunsaturated, branched or linear mono-, di-, tri-, or polyhydroxy hydrocarbon residue, a $C_2$ to $C_{30}$ saturated or mono- or polyunsaturated, branched or linear mono, di-, tri-, or polyamino hydrocarbon residue, with the provision that for the case in which $R^7$ and $R^8$ denote —OH and $R^9$ or $R^{10}$ simultaneously denotes hydrogen, the remaining group $R^9$ or $R^{10}$ does not denote a dihydroxyethyl residue.

In a particularly preferred embodiment of the teaching according to the present invention,
(R)-(−)-4-hydroxymethyl-γ-butyrolactone and/or
D,L-4-hydroxymethyl-γ-butyrolactone and/or
(S)-(+)-4-hydroxymethyl-γ-butyrolactone and/or
R-(−)-2-hydroxy-3,3-dimethyl-γ-butyrolactone and/or
D,L-2-hydroxy-3,3-dimethyl-γ-butyrolactone and/or
S(+)-2-hydroxy-3,3-dimethyl-γ-butyrolactone and/or
4-hydroxy-2,5-dimethyl-3(2H)-furanone and/or
tetrahydro-5-oxo-2-furancarboxylic acid and/or
tetrahydro-5-oxo-2-furancarboxylic acid, sodium salt and/or
tetrahydro-5-oxo-2-furancarboxylic acid, potassium salt and/or
2,5-dihydro-5-methoxy-2-furanone and/or
dihydro-3-hydroxy-4,4-dimethyl-2(3H)-furanone
are used as a compound corresponding to the formula (Fur-I). In a very particularly preferred embodiment of the teaching according to the present invention, dihydro-3-hydroxy-4,4-dimethyl-2(3H)-furanone is used as a compound corresponding to formula (Fur-I).

A further care-providing substance preferred for use, which possesses activating properties, is taurine. Cosmetic agents preferred according to the present invention include, based on their weight, 0.01 to 15 wt %, preferably 0.025 to 12.5 wt %, particularly preferably 0.05 to 10 wt %, more preferably 0.1 to 7.5 wt %, and in particular 0.5 to 5 wt % taurine (2-aminoethanesulfonic acid).

A further preferred group of care-providing substances in the agents according to the present invention are vitamins, provitamins, or vitamin precursors. These are described below:

The group of substances referred to as "vitamin A" includes retinol (vitamin $A_1$) as well as 3,4-didehydroretinol (vitamin $A_2$). β-Carotene is the provitamin of retinol. Vitamin A components that are suitable according to the present invention are, for example, vitamin A acid and esters thereof, vitamin A aldehyde, and vitamin A alcohol, as well as esters thereof such as the palmitate and acetate. The agents used according to the present invention include the vitamin A component preferably in quantities from 0.05 to 1 wt %, based on the total preparation.

Members of the vitamin B group or vitamin B complex are, among others:
- Vitamin $B_1$ (thiamine)
- Vitamin $B_2$ (riboflavin)
- Vitamin $B_3$. The compounds nicotinic acid and nicotinic acid amide (niacinamide) are often listed under this designation. Nicotinic acid amide is preferred according to the present invention; it is included in the agents used according to the present invention preferably in quantities from 0.05 to 1 wt % based on the total agent.
- Vitamin $B_5$ (pantothenic acid, panthenol, and pantolactone). In the context of this group, panthenol and/or pantolactone are preferably used (see below). Derivatives of panthenol that are usable according to the present invention are in particular esters and ethers of panthenol, and cationically derivatized panthenols. The aforesaid compounds of the vitamin $B_5$ type are included in the agents according to the present invention preferably in quantities from 0.05 to 10 wt % based on the total agent. Quantities from 0.1 to 5 wt % are particularly preferred.
- Vitamin $B_6$ (pyridoxine as well as pyridoxamine and pyridoxal).

Vitamin C (ascorbic acid). Vitamin C is employed in the agents according to the present invention preferably in quantities from 0.1 to 3 wt % based on the total agent. Utilization in the form of the palmitic acid ester, glucosides, or phosphates can be preferred. Utilization in combination with tocopherols can likewise be preferred.

Vitamin E (tocopherols, in particular □-tocopherol). Tocopherol and its derivatives, which include in particular esters such as the acetate, nicotinate, phosphate, and succinate, are included in the agents according to the present invention preferably in quantities from 0.05 to 1 wt % based on the total agent.

Vitamin F. The term "vitamin F" is usually understood to mean essential fatty acids, in particular linoleic acid, linolenic acid, and arachidonic acid.

Vitamin H. "Vitamin H" refers to the compound (3aS,4S, 6aR)-2-oxohexahydrothienol[3,4-d]-imidazole-4-valeric acid, for which the trivial name "biotin" has, however, now become established. Biotin is included in the agents according to the present invention preferably in quantities from 0.0001 to 1.0 wt %, in particular in quantities from 0.001 to 0.01 wt %.

In summary, those cosmetic agents according to the present invention which include, based on their weight, 0.1 to 5 wt %, preferably 0.2 to 4 wt %, particularly preferably 0.25 to 3.5 wt %, more preferably 0.5 to 3 wt %, and in particular 0.5 to 2.5 wt % vitamins and/or provitamins and/or vitamin precursors that are allocated preferably to the groups A, B, C, E, F, and H, are preferred; preferred agents include -(2,4-dihydroxy-N-(3-hydroxypropyl)-3,3-dimethylbutyramide, provitamin $B_5$) and/or panthothenic acid (vitamin $B_3$, vitamin $B_5$) and/or niacin, niacinamide or nicotinamide (vitamin $B_3$) and/or L-ascorbic acid (vitamin C) and/or thiamine (vitamin $B_1$) and/or riboflavin (vitamin $B_2$, vitamin G) and/or biotin (vitamin $B_7$, vitamin H) and/or folic acid (vitamin $B_9$, vitamin $B_c$ or vitamin M) and/or vitamin $B_6$ and/or vitamin $B_{12}$.

It has been found that specific quinones have a particular suitability as a care-providing substance. The agents according to the present invention can therefore include, as a further care-providing substance, 0.0001 to 5 wt % of at least one bioquinone of formula (Ubi)

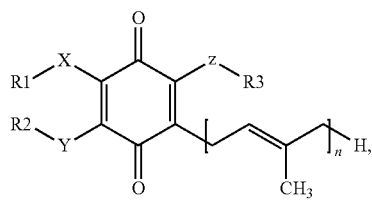
(Ubi)

in which

X, Y, Z mutually independently denote —O— or —NH— or —NR⁴— or a chemical bond,

R¹, R², R³ mutually independently denote a hydrogen atom or an optionally substituted aryl group or an optionally substituted ($C_1$ to $C_6$) alkyl group or a hydroxyalkyl group or a polyhydroxyalkyl group or an optionally substituted ($C_1$ to $C_6$) alkylene group, or a ($C_1$ to $C_6$) acyl group, wherein preferred residues are selected mutually independently from —H, —CH₃, —CH₂CH₃, —(CH₂)₂CH₂, —CH(CH₃)₂, —(CH₂)₃CH₃, —CH(CH₃)CH₂CH₃, —CH₂CH (CH₃)₂, —C(CH₃)₃, R⁴ denotes —CH₃, —CH₂CH₃, —(CH₂)₂CH₂, —CH(CH₃)₂, —(CH₂)₃CH₃, —CH(CH₃)CH₂CH₃, —CH₂CH(CH₃)₂, —C(CH₃)₃, n denotes values from 1 to 20, preferably from 2 to 15, and in particular 5, 6, 7, 8, 9, 10.

Particularly preferred cosmetic agents according to the present invention are characterized in that they include as a care-providing substance, based on their weight, 0.0001 to 1 wt %, preferably 0.001 to 0.5 wt %, and particularly preferably 0.005 to 0.1 wt % of at least one ubiquinone and/or at least one ubiquinol and/or at least one derivative of said substances, wherein preferred agents include a ubiquinone of formula (Ubi)

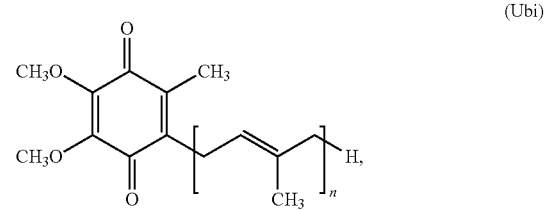
(Ubi)

in which n denotes the values 6, 7, 8, 9, or 10, particularly preferably 10 (Coenzyme Q10).

Alternatively or in addition to the particularly preferred ubiquinones, the agents according to the present invention can also include plastoquinones. Preferred agents according to the present invention are here characterized in that they include 0.0002 to 4 wt %, preferably 0.0005 to 3 wt %, particularly preferably 0.001 to 2 wt %, more preferably 0.0015 to 1, and in particular 0.002 to 0.5 wt % of at least one plastoquinone of formula (Ubi-b)

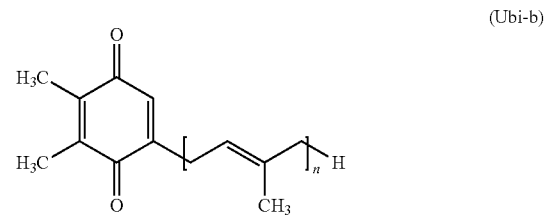
(Ubi-b)

in which n denotes values from 1 to 20, preferably from 2 to 15, and in particular 5, 6, 7, 8, 9, 10, wherein particularly preferred agents include plastoquinone PQ-9.

The agents according to the present invention can include ectoin as a further care enhancer. Ectoin ((4S)-2-methyl-1,4,5,6-tetrahydropyrimidine-4-carboxylic acid) is a natural substance belonging to the group of the compatible solutes. Cosmetic agents preferred according to the present invention are characterized in that they include, based on their weight, 0.001 to 10 wt %, preferably 0.01 to 5 wt %, particularly preferably 0.05 to 2.5 wt %, and in particular 0.1 to 1 wt % (S)-2-methyl-1,4,5,6-tetrahydro-4-pyrimidinecarboxylic acid (ectoin) as well as the physiologically acceptable salts of that compound, and/or (S,S)-5-hydroxy-2-methyl-1,4,5,6-tetrahydro-4-pyrimidinecarboxylic acid (hydroxyectoin) as well as the physiologically acceptable salts of that compound.

Allantoin is a further care-providing substance. In various animal species, principally in mammals, allantoin (5-ureidohydantoin, N-(2,5-dioxo-4-imidazolidinyl) urea) is, alongside uric acid, the end product of the breakdown of nucleic acids, especially of purine bases.

Allantoin is used is cosmetics in hair creams, sunblock agents, shaving lotions, in toothpaste, and in agents to counteract excessive perspiration (hyperhidrosis) and skin irritations. It brings about an acceleration in cell breakdown, cell formation, or cell regeneration, and soothes the skin. Healing of difficult-to-heal injuries is also assisted, although allantoin does not possess any antiseptic properties.

Particularly preferred cosmetic agents according to the present invention include, based on their weight, 0.001 to 10 wt %, preferably 0.01 to 5 wt %, particularly preferably 0.05 to 2.5 wt %, and in particular 0.1 to 1 wt % 5-ureidohydantoin (allantoin).

To improve the elasticity and strengthen the internal structure of hair treated with the agents according to the present invention, the agents according to the present invention can include purine and/or purine derivatives as a care-providing substance. In particular, the result of combining purine and/or purine derivatives with ubiquinones and/or plastoquinones as a care-providing substance is that hair treated with corresponding agents exhibits, inter alia, higher measured values in differential thermal analysis, and improved wet and dry combability values.

Purine (7H-imidazo[4,5-d]pyrimidine) does not occur in isolation in nature, but constitutes the basic member of the purines. Purines in turn are a group of important compounds, widespread in nature and involved in human, animal, plant, and microbial metabolic processes, that derive from the basic member by substitution with OH, $NH_2$, SH in the 2-, 6-, and 8-position, and/or with $CH_3$ in the 1-, 3-, 7 position. Purine can be manufactured, for example, from aminoacetonitrile and formamide. Purines and purine derivatives are often isolated as natural substances, but are also accessible synthetically by numerous routes.

Preferred agents according to the present invention include purine and/or purine derivatives in narrower quantity ranges. Cosmetic agents preferred according to the present invention are characterized here in that they include, based on their weight, 0.001 to 2.5 wt %, preferably 0.0025 to 1 wt %, particularly preferably 0.005 to 0.5 wt %, and in particular 0.01 to 0.1 wt % purine(s) and/or purine derivative(s).

Among purine, the purines, and the purine derivatives, some representatives are particularly preferred according to the present invention. Cosmetic agents preferred according to the present invention are characterized in that they include as a care-providing substance, based on their weight, 0.001 to 2.5 wt %, preferably 0.0025 to 1 wt %, particularly preferably 0.005 to 0.5 wt %, and in particular 0.01 to 0.1 wt % purine(s) and/or purine derivative(s), wherein preferred agents include purine and/or purine derivative(s) of the formula (Pur-I)

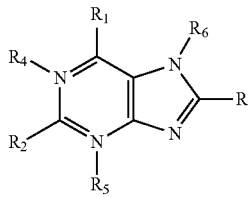

(Pur-I)

which the residues $R^1$, $R^2$, and $R^3$ are selected mutually independently from —H, —OH, $NH_2$, —SH, and the residues $R^4$, $R^5$, and $R^6$ are selected mutually independently from —H, —$CH_3$, and —$CH_2$—$CH_3$, the following compounds being preferred:

purine ($R^1$=$R^2$=$R^3$=$R^4$=$R^5$=$R^6$=H)
adenine ($R^1$=$NH_2$, $R^2$=$R^3$=$R^4$=$R^5$=$R^6$=H)
guanine ($R^1$=OH, $R^2$=$NH_2$, $R^3$=$R^4$=$R^5$=$R^6$=H)
uric acid ($R^1$=$R^2$=$R^3$=OH, $R^4$=$R^5$=$R^6$=H)
hypoxanthine ($R^1$=OH, $R^2$=$R^3$=$R^4$=$R^5$=$R^6$=H)
6-purinethiol ($R^1$=SH, $R^2$=$R^3$=$R^4$=$R^5$=$R^6$=H)
6-thioguanine ($R^1$=SH, $R^2$=$NH_2$, $R^3$=$R^4$=$R^5$=$R^6$=H)
xanthine ($R^1$=$R^2$=OH, $R^3$=$R^4$=$R^5$=$R^6$=H)
caffeine ($R^1$=$R^2$=OH, $R^3$=H, $R^4$=$R^5$=$R^6$=$CH_3$)
theobromine ($R^1$=$R^2$=OH, $R^3$=$R^4$=H, $R^5$=$R^6$=$CH_3$)
theophylline ($R^1$=$R^2$=OH, $R^3$=H, $R^4$=$CH_3$, $R^5$=$CH_3$, $R^6$=H).

It is further advantageous to use purine or purine derivatives and bioquinones at a specific ratio to one another. Preferred in this context are agents according to the present invention in which the weight ratio of purine (derivative(s)) to bioquinone(s) is equal to 10:1 to 1:100, preferably 5:1 to 1:50, particularly preferably 2:1 to 1:20, and in particular 1:1 to 1:10.

As already mentioned, caffeine is a particularly preferred purine derivative and Coenzyme Q10 is a particularly preferred bioquinone. Particularly preferred agents according to the present invention are therefore characterized in that they include, based on their weight, 0.001 to 2.5 wt %, preferably 0.0025 to 1 wt %, particularly preferably 0.005 to 0.5 wt %, and in particular 0.01 to 0.1 wt % caffeine, and 0.0002 to 4 wt %, preferably 0.0005 to 3 wt %, particularly preferably 0.001 to 2 wt %, more preferably 0.0015 to 1, and in particular 0.002 to 0.5 wt % Coenzyme Q10.

The agents according to the present invention can also include flavonoids as a care-providing substance. Flavonoids are a group of water-soluble vegetable dyes, and play an important role in the metabolism of many plants. Together with the phenolic acids, they belong to the polyphenols. Well over 6,500 different flavonoids are known, and can be subdivided into flavonols, flavones, flavanones, isoflavanoids, and anthocyans.

Flavonoids from all six groups can be used according to the present invention, specific representatives from the individual groups being preferred as a care-providing substance because of their particularly intense effect. Preferred flavonols are quercetin, rutin, camphor oil, myricetin, isorhamnetin, preferred flavanols are catechin, gallocatechin, epicatechin, epigallocatechin gallate, theaflavin, thearubigin, preferred flavones are luteolin, apigenin, morin, preferred flavanones are hesperetin, naringenin, eriodictyol, preferred isoflavanoids are genistein, daidzein, and preferred anthocyanidins (anthocyans) are cyanidin, delphinidin, malvidin, pelargonidin, peonidin, petunidin.

Cosmetic agents particularly preferred according to the present invention are characterized in that they include, based on their weight, 0.001 to 2.5 wt %, preferably 0.0025 to 1 wt %, particularly preferably 0.005 to 0.5 wt %, and in particular 0.01 to 0.1 wt % flavonoids, in particular flavonols, particularly preferably 3,3',4',5,7-pentahydroxyflavone (quercetin) and/or 3,3',4',5,7-pentahydroxyflavone-3-O-rutinoside (rutin).

The use of bisabolol and/or bisabolol oxides as a care-providing agent in the agents according to the present invention is also preferred. Cosmetic agents according to the present invention that additionally include 0.001 to 5 wt %, preferably 0.01 to 4 wt %, particularly preferably 0.02 to 2.5 wt %, and in particular 0.1 to 1.5 wt % bisabolol and/or oxides of bisabolol, preferably (−)-alpha-bisabolol, are preferred here.

Creatine is also suitable according to the present invention as a care-providing substance. Creatine (3-methylguanidinoacetic acid) is an organic acid that, inter alia, contributes to supplying muscles with energy in vertebrates. Creatine is synthesized in the kidneys, the liver, and the pancreas. It is derived formally from the amino acids glycine and arginine, and 95% of it is present in skeletal muscle.

Particularly preferred cosmetic agents according to the present invention include, based on their weight, 0.01 to 15 wt %, preferably 0.025 to 12.5 wt %, particularly preferably 0.05 to 10 wt %, more preferably 0.1 to 7.5 wt %, and in particular 0.5 to 5 wt % N-methylguanidinoacetic acid (creatine).

The agents according to the present invention can include, in addition to the ingredients recited above and optional further ingredients, further substances that prevent, mitigate, or cure hair loss. A content of hair-root-stabilizing active agents is particularly advantageous. These substances are described below:

Propecia (finasteride) is at present the only preparation that is approved worldwide and for which effectiveness and compatibility have been demonstrated in numerous studies. The effect of Propecia is that less DHT can form from testosterone.

Minoxidil, with or without supplementary additives, is probably the oldest demonstrably effective hair growth agent. For the treatment of hair loss, it must only be used for external application. Hair lotions exist that include 2% to 5% minoxidil, also gels having up to 15% minoxidil. Effectiveness increases with dosage, but minoxidil is soluble in hair lotions only up to a 5% proportion. In many countries, hair lotions having a minoxidil content of up to 2% are obtainable without a prescription.

To counteract hormonal influences on the hair follicles, spironolactone can be applied for external use in the form of a hair lotion and in combination with minoxidil. Spironolactone acts as an androgen receptor blocker, i.e. the binding of DHT to the hair follicles is prevented.

In summary, cosmetic agents according to the present invention that additionally include, based on its weight, 0.001 to 5 wt % hair-root-stabilizing substances, in particular minoxidil and/or finasteride and/or ketoconazole, are preferred.

The effect of additional anti-dandruff active substances (for example climbazole, piroctone olamine, or zinc pyrithione) is that the quantity of the yeast causing the dandruff is specifically reduced, the microbial flora returns to its normal percentage composition, and flaking is reduced to the natural level. Laboratory tests have demonstrated, however, that the different representatives of *Pityrosporum ovale* species exhibit different levels of reaction to the anti-dandruff active substances. A combination of anti-dandruff active substances is therefore most effective for maximum counteraction of all dandruff causes.

In summary, cosmetic agents according to the present invention that additionally include, based on their weight, 0.001 to 5 wt % anti-dandruff active substances, in particular piroctone olamine (1-hydroxy-4-methyl-6-(2,4,4-trimethylpentyl)pyridin-2(1H)-one, compound with 2-aminoethanol 1:1) and/or zinc pyrithione and/or selenium sulfide and/or climbazole and/or salicylic acid or fumaric acid, are preferred.

In addition to the care-providing substances, the agents according to the present invention can include further care-providing substances. Their presence is not obligatorily necessary in order for the effects according to the present invention to be achieved, but farther-reaching effects, such as a pleasant feel or pleasant application haptics, can result from the use of these care-providing substances.

The agents according to the present invention can, with particular preference, include one or more amino acids as a further ingredient. Amino acids particularly preferably usable according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-DOPA), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, wherein both the individual amino acids and mixtures can be used. Preferred agents according to the present invention include one or more amino acids in narrower quantity ranges. Cosmetic agents preferred according to the present invention are characterized here in that they include as a care-providing substance, based on their weight, 0.01 to 5 wt %, preferably 0.02 to 2.5 wt %, particularly preferably 0.05 to 1.5 wt %, more preferably 0.075 to 1 wt %, and in particular 0.1 to 0.25 wt % amino acid(s), preferably from the group of glycine and/or alanine. and/or valine and/or lysine and/or leucine and/or threonine.

As a further constituent, the agents according to the present invention can include at least one carbohydrate from the group of monosaccharides, disaccharides, and/or oligosaccharides. Cosmetic agents preferred according to the present invention are characterized here in that they include as a care-providing substance, based on their weight, 0.01 to 5 wt %, preferably 0.05 to 4.5 wt %, particularly preferably 0.1 to 4 wt %, more preferably 0.5 to 3.5 wt %, and in particular 0.75 to 2.5 wt % carbohydrate(s) selected from monosaccharides, disaccharides, and/or oligosaccharides, wherein preferred carbohydrates are selected from monosaccharides, in particular D-ribose and/or D-xylose and/or L-arabinose and/or D-glucose and/or D-mannose and/or D-galactose and/or D-fructose and/or sorbose and/or L-fucose and/or L-rhamnose, disaccharides, in particular sucrose and/or maltose and/or lactose and/or trehalose and/or cellobiose and/or gentobiose and/or isomaltose.

Particularly preferred agents according to the present invention include, based on their weight,
  0.005 to 0.015 wt % caffeine and 0.75 to 1.5 wt % glucose monohydrate,
  0.005 to 0.015 wt % caffeine and 0.75 to 1.5 wt % sucrose,
  0.005 to 0.015 wt % caffeine and 0.75 to 1.5 wt % fructose.

As already mentioned, preferred agents according to the present invention include (an) amino acids(s).

Amino acids particularly preferably usable according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-cyss), L-carnitine, L-citrulline, L-theanine, 3',4'-dihydroxy-L-phenylalanine (L-DOPA), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, wherein both the individual amino acids and mixtures can be used.

Preferred agents according to the present invention include one or more amino acids in narrower quantity ranges. Cosmetic agents preferred according to the present invention are characterized here in that they additionally include 0.05 to 5 wt %, preferably 0.1 to 2.5 wt %, particularly preferably 0.15 to 1 wt %, and in particular 0.2 to 0.5 wt % amino acid(s), preferably (an) amino acid(s) from the group of glycine and/or alanine and/or valine and/or lysine and/or leucine and/or threonine.

Particularly preferred agents according to the present invention include, based on their weight, 0.005 to 0.015 wt % caffeine and 0.75 to 1.5 wt % glucose monohydrate and 0.1 to 0.25 wt % glycine,
0.005 to 0.015 wt % caffeine and 0.75 to 1.5 wt % sucrose and 0.1 to 0.25 wt % glycine,
0.005 to 0.015 wt % caffeine and 0.75 to 1.5 wt % fructose and 0.1 to 0.25 wt % glycine,
0.005 to 0.015 wt % caffeine and 0.75 to 1.5 wt % glucose monohydrate and 0.1 to 0.25 wt % alanine,
0.005 to 0.015 wt % caffeine and 0.75 to 1.5 wt % sucrose and 0.1 to 0.25 wt % alanine,
0.005 to 0.015 wt % caffeine and 0.75 to 1.5 wt % fructose and 0.1 to 0.25 wt % alanine,
0.005 to 0.015 wt % caffeine and 0.75 to 1.5 wt % glucose monohydrate and 0.1 to 0.25 wt % valine,
0.005 to 0.015 wt % caffeine and 0.75 to 1.5 wt % sucrose and 0.1 to 0.25 wt % valine,
0.005 to 0.015 wt % caffeine and 0.75 to 1.5 wt % fructose and 0.1 to 0.25 wt % valine.

The 4-morpholinomethyl-substituted silicones employed according to the present invention can of course be used together with further conventional silicones.

Agents particularly preferred according to the present invention include the further silicone(s) preferably in quantities from 0.1 to 10 wt %, preferably from 0.25 to 7 wt %, and in particular from 0.5 to 5 wt %, based in each case on the total agent.

Preferred silicones are described below.

Particularly preferred agents according to the present invention are characterized in that they include at least one silicone of formula (Si-I)

$$(CH_3)_3Si—[O—Si(CH_3)_2]_x—O—Si(CH_3)_3 \quad (Si\text{-}I),$$

in which x denotes a number from 0 to 100, preferably from 0 to 50, more preferably from 0 to 20, and in particular 0 to 10.

These silicones are referred to according to INCI nomenclature as Dimethicones.

The compounds recited in page 57 of the priority document are preferably employed in the context of the present invention as a silicone of formula Si-I, wherein $(CH_3)_3Si—O—Si(CH_3)_3$, $(CH_3)_3Si—O—(CH_3)_2Si—O—Si(CH_3)_3$, and/or $(CH_3)_3Si—[O—(CH_3)_2Si]_2—O—Si(CH_3)_3$ are particularly preferred.

Mixtures of the silicones recited above can of course also be included in the agents according to the present invention.

Preferred silicones usable according to the present invention have viscosities from 0.2 to 2 mm²s⁻¹ at 20° C.; silicones having viscosities from 0.5 to 1 mm²s⁻¹ are particularly preferred.

Particularly preferred agents according to the present invention include one or more aminofunctional silicones. Such silicones can be described, for example, by the formula

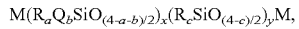

wherein in the above formula, R is a hydrocarbon or a hydrocarbon residue having 1 to approximately 6 carbon atoms, Q is a polar residue of the general formula —R¹HZ, in which R¹ is a divalent connecting group that is bound to hydrogen and to the Z residue, assembled from carbon and hydrogen atoms, carbon, hydrogen, and oxygen atoms, or carbon, hydrogen, and nitrogen atoms, and Z is an organic aminofunctional residue that includes at least one aminofunctional group; "a" assumes values in the range from approximately 0 to approximately 2, "b" assumes values in the range from approximately 1 to approximately 3, "a"+"b" is less than or equal to 3, and "c" is a number in the range from approximately 1 to approximately 3, and x is a number in the range from 1 to approximately 2,000, preferably from approximately 3 to approximately 50, and most preferably from approximately 3 to approximately 25, and y is a number in the range from approximately 20 to approximately 10,000, preferably from approximately 125 to approximately 10,000, and most preferably from approximately 150 to approximately 1,000, and M is a suitable silicone terminal group as known in the existing art, preferably trimethylsiloxy. Non-limiting examples of the residues represented by R include alkyl residues such as methyl, ethyl, propyl, isopropyl, isopropyl, butyl, isobutyl, amyl, isoamyl, hexyl, isohexyl and the like; alkenyl residues such as vinyl, halovinyl, alkylvinyl, allyl, haloallyl, alkylallyl; cycloalkyl residues such as cyclobutyl, cyclopentyl, cyclohexyl and the like; phenyl residues, benzyl residues, halogenated hydrocarbon residues such as 3-chloropropyl, 4-bromobutyl, 3,3,3-trifluoropropyl, chlorocyclohexyl, bromophenyl, chlorophenyl, and the like, as well as sulfur-containing residues such as mercaptoethyl, mercaptopropyl, mercaptohexyl, mercaptophenyl and the like; R is preferably an alkyl residue that includes 1 to approximately 6 carbon atoms, and R is most preferably methyl. Examples of R¹ include methylene, ethylene, propylene, hexamethylene, decamethylene, —CH₂CH(CH₃)CH₂—, phenylene, naphthylene, —CH₂CH₂SCH₂CH₂—, —CH₂CH₂OCH₂—, —OCH₂CH₂—, —OCH₂CH₂CH₂—, —CH₂CH(CH₃)C(O)OCH₂—, —(CH₂)₃CC(O)OCH₂CH₂—, —C₆H₄C₆H₄—, —C₆H₄CH₂C₆H₄—, and —(CH₂)₃C(O)SCH₂CH₂—.

Z is an organic aminofunctional residue including at least one functional amino group. One possible formula for Z is $NH(CH_2)_zNH_2$, in which z is 1 or more. Another possible formula for Z is $—NH(CH_2)_z(CH_2)_{zz}NH$, in which both z and zz are mutually independently 1 or more; this structure comprises diamino ring structures such as piperazinyl. Z is most preferably a —NHCH₂CH₂NH₂ residue. Another possible formula for Z is $—N(CH_2)_z(CH_2)_{zz}NX_2$ or —NX₂, in which each X is selected, independently of X₂, from the group consisting of hydrogen and alkyl groups having 1 to 12 carbon atoms, and zz is 0.

Q is most preferably a polar aminofunctional residue of the formula —CH₂CH₂CH₂NHCH₂CH₂NH₂. In the formulas, "a" assumes values in the range from approximately 0 to approximately 2, "b" assumes values in the range from approximately 2 to approximately 3, "a"+"b" is less than or equal to 3, and "c" is a number in the range from approximately 1 to approximately 3. The molar ratio of the $R_aQ_b SiO_{(4-a-b)/2}$ units to the $R_cSiO_{(4-c)/2}$ units is in the range from approximately 1:2 to 1:65, preferably from approximately 1:5 to approximately 1:65, and most preferably from approximately 1:15 to approximately 1:20. If one or more silicones of the above formula are used, the different variable substituents in the above formula can then be different in the different silicone components that are present in the silicone mixture.

Preferred agents according to the present invention are characterized in that an aminofunctional silicone of formula (Si-II)

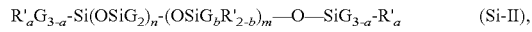

is included, in which
G is —H, a phenyl group, —OH, —O—CH₃, —CH₃, —O—CH₂CH₃, —CH₂CH₃, —O—CH₂CH₂CH₃, —CH₂CH₂CH₃, —O—CH(CH₃)₂, —CH(CH₃)₂, —O—CH₂CH₂CH₂CH₃, —CH₂CH₂CH₂CH₃, —O—CH₂CH(CH₃)₂, —CH₂CH(CH₃)₂, —O—CH(CH₃)CH₂CH₃, —CH(CH₃)CH₂CH₃, —O—C(CH₃)₃, —C(CH₃)₃;

a denotes a number between 0 and 3, in particular 0;
b denotes a number between 0 and 1, in particular 1,
m and n are numbers whose sum (m+n) is between 1 and 2000, preferably between 50 and 150, wherein n preferably assumes values from 0 to 1999 and in particular from 49 to 149, and m preferably assumes values from 1 to 2000, in particular from 1 to 10;
R' is a monovalent residue selected from
-Q-N(R'')—CH$_2$—CH$_2$—N(R'')$_2$,
-Q-N(R'')$_2$,
-Q-N$^+$(R'')$_3$A$^-$,
-Q-N$^+$H(R'')$_2$A$^-$,
-Q-N$^+$H$_2$(R'')A$^-$,
-Q-N(R'')—CH$_2$—CH$_2$—N$^+$R''H$_2$A$^-$,
wherein each Q denotes a chemical bond, —CH$_2$—, —CH$_2$—CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—, R'' denotes identical or different residues from the group of —H, phenyl, benzyl, CH$_2$—CH(CH$_3$)Ph, C$_{1-20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion that is preferably selected from chloride, bromide, iodide, or methosulfate.

Particularly preferred agents according to the present invention are characterized in that they include at least one aminofunctional silicone of formula (Si-IIa)

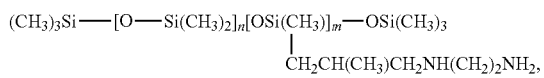

(Si-IIa)

in which m and n are numbers whose sum (m+n) is between 1 and 2000, preferably between 50 and 150, wherein n assumes values preferably from 0 to 1999 and in particular from 49 to 149, and m preferably assumes values from 1 to 2000, in particular from 1 to 10.

These silicones are referred to according to the INCI declaration as Trimethylsilylamodimethicones.

Also particularly preferred are agents according to the present invention that include an aminofunctional silicone of formula (Si-IIb)

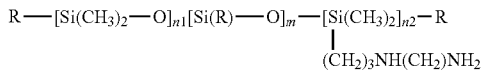

(Si-IIb)

in which R denotes —OH, —O—CH$_3$, or a —CH$_3$ group, and m, n1, and n2 are numbers whose sum (m+n1+n2) is between 1 and 2000, preferably between 50 and 150, wherein the sum (n1+n2) assumes values preferably from 0 to 1999 and in particular from 49 to 149, and m assumes values preferably from 1 to 2000, in particular from 1 to 10.

These silicones are referred to according to the INCI declaration as Amodimethicone.

Regardless of which aminofunctional silicones are employed, agents according to the present invention that include an aminofunctional silicone whose amine number is above 0.25 meq/g, preferably above 0.3 meq/g, and in particular above 0.4 meq/g, are preferred. The amine number denotes, in this context, the milliequivalent of amine per gram of the aminofunctional silicone. It can be ascertained by titration, and also indicated using the unit of "mg KOH/g".

Agents preferred according to the present invention are characterized in that they include, based on their weight, 0.01 to 10 wt %, preferably 0.1 to 8 wt %, particularly preferably 0.25 to 7.5 wt %, and in particular 0.5 to 5 wt % aminofunctional silicone(s).

The cyclic dimethicones referred to according to INCI as Cyclomethicones are also usable with preference according to the present invention. Agents according to the present invention that include at least one silicone of formula Si-III

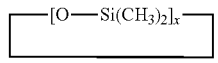

(Si-III)

in which x denotes a number from 3 to 200, preferably from 3 to 10, more preferably from 3 to 7, and in particular 3, 4, 5, or 6, are preferred here.

The silicones described above comprise a backbone that is constructed from —Si—O—Si— units. These —Si—O—Si— units can of course also be interrupted by carbon chains. Corresponding molecules are accessible via chain lengthening reactions, and are employed preferably in the form of silicone-in-water emulsions.

Agents likewise preferred according to the present invention are characterized in that they include at least one silicone of formula (Si-IV)

$$R_3Si—[O—SiR_2]_x—(CH_2)_n—[O—SiR_2]_y—O—SiR_3 \quad \text{(Si-IV)},$$

in which R denotes identical or different residues from the group —H, phenyl, benzyl, —CH$_2$—CH(CH$_3$)Ph, C$_{1-20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, x and y respectively denote a number from 0 to 200, preferably from 0 to 10, more preferably from 0 to 7, and in particular 0, 1, 2, 3, 4, 5, or 6, and n denotes a number from 0 to 10, preferably from 1 to 8, and in particular 2, 3, 4, 5, 6.

The silicones are preferably water-soluble. Agents preferred according to the present invention are characterized in that they include at least one water-soluble silicone.

The agents according to the present invention can include as a further ingredient at least one proteolipid of formula (P-I)

$$R'—X—R'' \quad \text{(P-1)},$$

in which
R' denotes a straight-chain or branched, saturated or unsaturated hydrocarbon residue having 11 to 24 carbon atoms,
R'' signifies a protein, a peptide, or a protein hydrolysate,
X denotes —C(O)O— or —N$^+$(R$^{III}$$_2$)R$^{IV}$— or —N(R$^{III}$)R$^{IV}$— or —C(O)—N(R$^V$)R$^{VI}$—,
R$^{III}$ signifies —(CH$_2$)$_x$—CH$_3$ where x=0 to 22, and
R$^{IV}$ signifies —CH$_2$—CH(OH)—CH$_2$— or —(CH$_2$)$_x$— where x=0 to 22;
R$^V$ and R$^{VI}$ mutually independently denote —H or —(CH$_2$)$_x$—CH$_3$ where x=0 to 22,
with the provision that R'' denotes keratin or a keratin hydrolysate when X denotes C—(O)O—

Proteolipids are preferably used within specific quantities in the agents according to the present invention. Preferred cosmetic agents according to the present invention include, based on their weight, 0.01 to 10 wt %, preferably 0.02 to 5 wt %, particularly preferably 0.05 to 2.5 wt %, more preferably 0.1 to 1 wt %, and in particular 0.15 to 0.5 wt % proteolipid(s).

The residue R" in formula (P-I) denotes a peptide or a protein or a protein hydrolysate. When X=—C(O)O—, R" is selected from the group of keratin or keratin hydrolysate.

Preferred residues R" are oligopeptides that comprise at least one amino acid sequence Glu-Glu-Glu, wherein the amino group can be present in free or protonated form, and the carboxy groups can be present in free or deprotonated form.

In this as in all subsequent formulas, the bracketed hydrogen atom of the amino group, like the bracketed hydroxy group of the acid function, signifies that the relevant groups can be present as such (this then refers to an oligopeptides having the relevant number of amino acids, as depicted in formula 3 above), or that the amino acid sequence is present in an oligopeptide that also comprises further amino acids; depending on where the further amino acid(s) is/are bound, the bracketed constituents of the aforementioned formulas are replaced by the further amino acid residue(s).

"Oligopeptides" for purposes of the present application are condensation products, linked in acid-amide fashion by peptide bonds, of amino acids, which comprise at least 3 and at most 25 amino acids.

In hair treatment agents preferred according to the present invention of the embodiment described above, the oligopeptide (=residue R") comprises 5 to 15 amino acids, preferably 6 to 13 amino acids, particularly preferably 7 to 12 amino acids, and in particular 8, 9, or 10 amino acids.

The molar mass of the proteolipid included in the agents according to the present invention can vary depending on whether further amino acids are bound to the Glu-Glu-Glu sequence and on the nature of those amino acids, and as a function of the selection of the residues R' and optionally $R^{III}$ and $R^{IV}$. Cosmetic agents preferred according to the present invention are characterized in that the proteolipid has a molar mass from 1000 to 30,000 Da, preferably from 1250 to 25,000 Da, particularly preferably from 1500 to 20,000 Da, and in particular from 2000 to 15,000 Da.

It is preferred to select as the residue R" oligopeptides that are not made up only of the three glutamic acids, but comprise further amino acids bound to that sequence. These further amino acids are preferably selected from specific amino acids, while specific other representatives are less preferred according to the present invention.

It is thus preferred if the residue R" of the proteolipids employed in the agents according to the present invention includes no methionine. It is further preferred if the residue R" of the proteolipids employed in the agents according to the present invention includes no cysteine and/or cystine.

It is further preferred if the residue R" of the proteolipids employed in the agents according to the present invention includes no aspartic acid and/or asparagine. It is further preferred if the residue R" of the proteolipids employed in the agents according to the present invention includes no serine and/or threonine.

Conversely, it is preferred if the residue R" of the proteolipids employed in the agents according to the present invention includes tyrosine. It is further preferred if the residue R" of the proteolipids employed in the agents according to the present invention includes leucine. It is further preferred if the residue R" of the proteolipids employed in the agents according to the present invention includes isoleucine. It is further preferred if the residue R" of the proteolipids employed in the agents according to the present invention includes arginine. It is further preferred if the residue R" of the proteolipids employed in the agents according to the present invention includes valine.

Oligopeptides particularly preferred as residue R", or amino acid sequences included in the preferred oligopeptides, are described below:

A particularly preferred oligopeptide additionally includes tyrosine, which is bound preferably via its acid function to the Glu-Glu-Glu sequence. Cosmetic agents preferred according to the present invention are therefore characterized in that the oligopeptide included as residue R" in the proteolipids of formula (I) comprises at least one Tyr-Glu-Glu-Glu amino acid sequence, wherein the amino group can be present in free or protonated form, and the carboxy groups can be present in free or deprotonated form.

A further particularly preferred oligopeptide additionally includes isoleucine, which is bound preferably via its amino function to the Glu-Glu-Glu sequence. Cosmetic agents preferred according to the present invention are therefore characterized in that the oligopeptide included as residue R" in the proteolipids of formula (I) comprises at least one Glu-Glu-Glu-Ile amino acid sequence, wherein the amino group can be present in free or protonated form, and the carboxy groups can be present in free or deprotonated form.

Oligopeptides that comprise the two aforesaid amino acids (tyrosine and isoleucine) are preferred according to the present invention. Particularly preferred in this context are hair treatment agents according to the present invention in which the oligopeptide included as residue R" in the proteolipids of formula (I) comprises at least one Tyr-Glu-Glu-Glu-Ile amino acid sequence, wherein the amino group can be present in free or protonated form, and the carboxy groups can be present in free or deprotonated form.

Further preferred oligopeptides additionally contain arginine that is preferably present bound to isoleucine. Cosmetic agents preferred according to the present invention are therefore characterized in that the oligopeptide included as residue R" in the proteolipids of formula (I) comprises at least one Tyr-Glu-Glu-Glu-Ile-Arg amino acid sequence, wherein the amino groups can be present in free or protonated form, and the carboxy groups can be present in free or deprotonated form.

Even further preferred oligopeptides additionally include valine that is preferably present bound to arginine. Cosmetic agents further preferred according to the present invention are therefore characterized in that the oligopeptide included as residue R" in the proteolipids of formula (I) comprises at least one Tyr-Glu-Glu-Glu-Ile-Arg-Val amino acid sequence, wherein the amino groups can be present in free or protonated form, and the carboxy groups can be present in free or deprotonated form.

Even further preferred oligopeptides additionally include leucine that is preferably present bound to valine. Cosmetic agents further preferred according to the present invention are characterized in that the oligopeptide included as residue R" in the proteolipids of formula (I) comprises at least one Tyr-Glu-Glu-Glu-Ile-Arg-Val-Leu amino acid sequence, wherein the amino groups can be present in free or protonated form, and the carboxy groups can be present in free or deprotonated form.

Particularly preferred oligopeptides additionally include leucine that is preferably present bound to tyrosine. Cosmetic agents further preferred according to the present invention are characterized in that the oligopeptide included as residue R" in the proteolipids of formula (I) comprises at least one Leu-Tyr-Glu-Glu-Glu-Ile-Arg-Val-Leu amino acid sequence, wherein the amino groups can be present in free or protonated form, and the carboxy groups can be present in free or deprotonated form.

In summary, cosmetic agents according to the present invention that include at least one proteolipid of formula (I) in which R'' comprises at least one Leu-Tyr-Glu-Glu-Glu-Ile-Arg-Val-Leu amino acid sequence, wherein the amino groups can be present in free or protonated form, and the carboxy groups can be present in free or deprotonated form, are particularly preferred.

As already mentioned, R'' is selected from the group of keratin or keratin hydrolysate when X=—C(O)O—. In all other cases, the residue R'' in formula (P-I) can denote a peptide or a protein or a protein hydrolysate, wherein protein hydrolysates are preferred. Protein hydrolysates are product mixtures that are obtained by the acid-, base-, or enzyme-catalyzed breakdown of proteins. Protein hydrolysates of both vegetable and animal origin can be used according to the present invention.

Animal protein hydrolysates are, for example, protein hydrolysates of elastin, collagen, keratin, silk, and milk protein, which can also be present in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), and Kerasol® (Croda).

It is preferred according to the present invention to use protein hydrolysates of vegetable origin, for example soy, almond, rice, pea, potato, and wheat protein hydrolysates. Such products are obtainable, for example, under the trademarks Gluadin® (Cognis), DiaMin® (Diamalt), Lexein® (Inolex), and Crotein® (Croda).

The residue R'' is preferably selected from keratin or keratin hydrolysates regardless of the selection of X in formula (P-I). Preferred cosmetic agents according to the present invention are characterized in that they include at least one proteolipid of formula (P-I) in which R'' denotes keratin or a keratin hydrolysate.

Cosmetic agents according to the present invention that include at least one proteolipid of formula (P-I) in which $R^{III}$ signifies —$CH_3$ and $R^{IV}$ denotes —$(CH_2)_x$—, where x=0, 1, 2, 3, 4, 5, 6, 7, 8, are particularly preferred.

Particularly preferred cosmetic agents according to the present invention are further characterized in that they include at least one proteolipid of formula (I) in which X denotes —$N^+(CH_3)_2$—$CH_2$—CH(OH)—$CH_2$, and R' denotes —$(CH_2)_{17}$—$CH_3$.

Further preferred cosmetic agents according to the present invention are likewise characterized in that they include at least one proteolipid of formula (P-I) in which X denotes —C(O)O— and R' denotes —$(CH_2)_{17}$—$CH_3$.

It has proven to be advantageous to use, in addition to the proteolipids, protein hydrolysates. The latter intensify the action of the proteolipids and are in turn intensified in terms of their effects. Protein hydrolysates have been described in detail above as residue R''. In summary, cosmetic agents according to the present invention that additionally include, based on their weight, 0.01 to 10 wt %, preferably 0.05 to 7 wt %, particularly preferably 0.1 to 5 wt %, more preferably 0.25 to 2.5 wt %, and in particular 0.5 to 2.0 wt % protein hydrolysate(s), preferably keratin hydrolysate(s), are preferred.

For aesthetic reasons, "clear" products are often preferred by consumers. Cosmetic agents preferred according to the present invention are therefore characterized in that they are transparent or translucent.

"Transparent or translucent" is understood in the context of the present invention as a composition that has an NTU value below 100. The NTU value (nephelometric turbidity unit) is a unit used in water treatment for turbidity measurements in liquids. It is the unit of the turbidity of a liquid, measured with a calibrated nephelometer.

In a preferred embodiment of the invention, an agent according to the present invention can furthermore also include UV filters (I). The UV filters to be used according to the present invention are not subject to any general restrictions in terms of their structure and their physical properties. Instead, all UV filters usable in the cosmetics sector, whose absorption maximum lies in the UVA (315 to 400 nm), UVB (280 to 315 nm), or UVC (<280 nm) regions, are suitable. UV filters having an absorption maximum in the UVB region, in particular in the region from approximately 280 to approximately 300 nm, are particularly preferred.

The UV filters used according to the present invention can be selected, for example, from substituted benzophenones, p-aminobenzoic acid esters, diphenylacrylic acid esters, cinnamic acid esters, salicylic acid esters, benzimidazoles, and o-aminobenzoic acid esters.

The UV filters (I) are included in the agents according to the present invention usually in quantities from 0.1 to 5 wt % based on the entire agent. Quantities from 0.4 to 2.5 wt % are preferred.

The agents according to the present invention can furthermore include a 2-pyrrolidone-5-carboxylic acid and derivatives thereof (J). The sodium, potassium, calcium, magnesium, or ammonium salts, in which the ammonium ion carries one to three $C_1$ to $C_4$ alkyl groups in addition to hydrogen, are preferred. The sodium salt is very particularly preferred. The quantities used in the agents according to the present invention are preferably 0.05 to 10 wt % based on the entire agent, particularly preferably 0.1 to 5, and in particular 0.1 to 3 wt %.

It can additionally prove to be advantageous if penetration adjuvants and/or swelling agents (M) are included in the agents according to the present invention. To be included thereamong are, for example, urea and urea derivatives, guanidine and derivatives thereof, arginine and derivatives thereof, water glass, imidazole and derivatives thereof, histidine and derivatives thereof, benzyl alcohol, glycerol, glycol and glycol ethers, propylene glycol and propylene glycol ethers, for example propylene glycol monoethyl ether, carbonates, hydrogen carbonates, diols and triols and in particular 1,2-diols and 1,3-diols such as 1,2-propanediol, 1,2-pentanediol, 1,2-hexanediol, 1,2-dodecanediol, 1,3-propanediol, 1,6-hexanediol, 1,5-pentanediol, 1,4-butanediol.

In addition, for purposes of the invention short-chain carboxylic acids (N) can advantageously additionally assist the active agent complex (A). "Short-chain carboxylic acids" and derivatives thereof are understood for purposes of the invention as carboxylic acids that can be saturated or unsaturated and/or straight-chain or branched or cyclic and/or aromatic and/or heterocylic, and have a molecular weight of less than 750. Saturated or unsaturated straight-chain or branched carboxylic acids having a chain length from 1 to 16 carbon atoms in the chain can be preferred for purposes of the invention; those having a chain length from 1 to 12 carbon atoms in the chain are very particularly preferred.

The short-chain carboxylic acids for purposes of the invention can comprise one, two, three, or more carboxy groups. Carboxylic acids having multiple carboxy groups, in particular di- and tricarboxylic acids, are preferred for purposes of the invention. The carboxy groups can be present entirely or partly as an ester, acid anhydride, lactone, amide, imidic acid, lactam, lactim, dicarboximide, carbohydrazide, hydrazone, hydroxam, hydroxime, amidine, amidoxime, nitrile, phosphonic ester, or phosphate ester. The carboxylic acids used according to the present invention can of course be substituted along the carbon chain or along the ring structure. To be included among the substituents of the carboxylic acids used according to the present invention are, for example, C1 to C8 alkyl, C2 to C8 alkenyl, aryl, aralkyl, and aralkenyl, hydroxymethyl, C2 to C8 hydroxyalkyl, C2 to C8 hydroxyalkenyl, aminomethyl, C2 to C8 aminoalkyl, cyano, formyl, oxo, thioxo, hydroxy, mercapto, amino, carboxy, or imino groups. Preferred substituents are C1 to C8 alkyl, hydroxymethyl, hydroxy, amino, and carboxy groups. Substituents in the alpha-position are particularly preferred. Very particularly preferred substituents are hydroxy, alkoxy, and amino groups, wherein the amino function can optionally be further substituted with alkyl, aryl, aralkyl, and/or alkenyl residues. In addition, the phosphonic esters and phosphate esters are likewise preferred carboxylic acid derivatives.

In a further preferred embodiment the agents according to the present invention can include emulsifier agents (F). The agents according to the present invention include emulsifier agents preferably in quantities from 0.1 to 25 wt %, in particular 0.5 to 15 wt %, based on the entire agent.

The compositions according to the present invention can preferably include at least one nonionogenic emulsifier agent having an HLB value from 8 to 18. Nonionogenic emulsifier agents having an HLB value from 10 to 15 can be particularly preferred according to the present invention.

It has been shown to be additionally advantageous if, in addition to the polymer(s) from the group of the cationic and/or amphoteric polymers, further polymers (G) are included in the agents according to the present invention. In a preferred embodiment, further polymers are therefore added to the agents according to the present invention, both anionic and nonionic polymers having proven effective.

It is also possible according to the present invention for the preparations to include multiple, in particular two different polymers of the same charge, and/or respectively one ionic and one amphoteric and/or nonionic polymer.

The further polymers (G) are included in the agents according to the present invention preferably in quantities from 0.05 to 10 wt % based on the total agent. Quantities from 0.1 to 5, in particular from 0.1 to 3 wt %, are particularly preferred.

A further subject of the present invention is a method for treating keratinic fibers, in which method a hair treatment agent according to the present invention is applied onto the keratinic fibers and is rinsed out again after a contact time from a few seconds to as much as 45 minutes.

The statements made regarding the agents according to the present invention apply mutatis mutandis with reference to preferred embodiments of the method according to the present invention.

A further subject of the present invention is the use of hair treatment agents according to the present invention
  to condition keratinic substances, and/or
  to improve the looseness, softness, shine, and/or combability and facilitate the styling of keratinic substances, and/or
  to improve retention of the conditioning effect in the context of hair washing, and/or
  to improve wet and dry combability, and/or
  to improve shine, and/or
  to improve the moisture budget of keratinic fibers, and/or
  to protect the keratinic fibers from oxidative damage, and/or
  to prevent grease re-absorption by keratinic fibers, and/or
  to enhance the washing fastness of colored keratinic fibers.

The statements made regarding the agents according to the present invention also apply mutatis mutandis with reference to preferred embodiments of the uses according to the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic composition including, in a cosmetically acceptable medium, at least one thickening agent and at least one 4-morpholinomethyl-substituted silicone of formula (V)

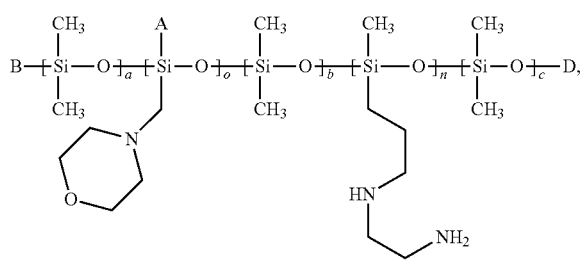

(V)

in which

A denotes a structural unit (I), (II), or (III) bound via —O—

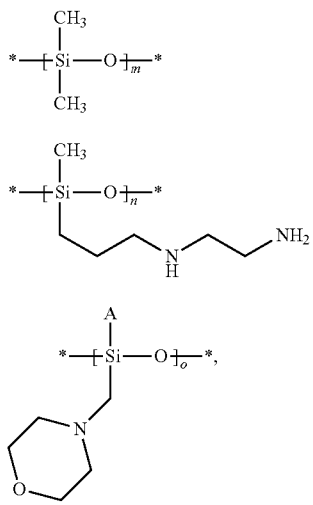

or an oligomeric or polymeric residue bound via —O— containing structural units of formulas (I), (II), or (III), or half of an oxygen atom connecting to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

2. The cosmetic composition according to claim 1, wherein the at least one 4-morpholinomethyl-substituted silicone is characterized such that m>(n+o) or (a+b+c)>(n+o).

3. The cosmetic composition according to claim 1, wherein the at least one 4-morpholinomethyl-substituted silicone(s) is included in the composition at a concentration of 0.00001 to 10 wt %.

4. The cosmetic composition according to claim 1, further comprising, based on its weight, 0.00001 to 5 wt % of a nonionic compound selected from the group consisting of branched ethoxylated tridecanol (INCI name: Trideceth-5), α-isotridecyl-ω-hydroxypolyglycol ether (INCI name: Trideceth-10), and mixtures thereof.

5. The cosmetic composition according to claim 1, wherein the at least one hydroxy-terminated 4-morpholinomethyl-substituted silicone(s) has a molar ratio of hydroxy to alkoxy in the range from 0.2:1 to 0.4:1.

6. The cosmetic composition according to claim 1, wherein the weight-average molar mass of the at least one 4-morpholinomethyl-substituted silicone of formula (V) is in the range from 2000 to 1,000,000 gmol$^{-1}$.

7. The cosmetic composition according to claim 1, wherein the at least one 4-morpholinomethyl-substituted silicone of formula (V) is present in the form of an oil-in-water emulsion in which the number-average size of the silicone particles in the emulsion is in the range from 3 to 500 nm.

8. The cosmetic composition according to claim 1, wherein the thickening agents are selected from the group consisting of:

(i.) associative thickening agents;
(ii.) crosslinked homopolymers of acrylic acid;
(iii.) crosslinked copolymers of (meth)acrylic acid and alkyl (C$_{1-6}$) acrylate;
(iv.) nonionic homopolymers and copolymers that contain monomers having an ethylenically unsaturated bond of the ester type and/or amide type;
(v.) homopolymers of ammonium acrylate or copolymers of ammonium acrylate and acrylamide;
(vi.) polysaccharides;
(vii.) fatty alcohols with C$_{12-30}$; and
(viii.) fatty acid amides.

9. The cosmetic composition according to claim 8, wherein the associative thickening agent is an associative polymer that is selected from the group consisting of (i.) nonionic amphiphilic polymers that include at least one fat chain and at least one hydrophilic unit;
(ii.) anionic amphiphilic polymers that include at least one hydrophilic unit and at least one unit having a fat chain;
(iii.) cationic amphiphilic polymers that include at least one hydrophilic unit and at least one unit having a fat chain; and
(iv.) amphoteric amphiphilic polymers that include at least one hydrophilic unit and at least one unit having a fat chain, wherein the fat chains comprise 10 to 30 carbon atoms.

10. The cosmetic composition according to claim 8, wherein the nonionic amphiphilic polymers that include at least one fat chain and at least one hydrophilic unit are selected from the group consisting of
(1) celluloses that are modified with groups that comprise at least one fat chain;
(2) hydroxypropyl guar compounds that are modified with groups that comprise at least one fat chain;
(3) urethane polyethers that include at least one alkyl or alkenyl group having 10 to 30 carbon atoms;
(4) copolymers of vinylpyrrolidone and hydrophobic monomers having a fat chain;
(5) copolymers of alkyl ($C_{1-6}$) methacrylates or alkyl ($C_{1-6}$) acrylates and amphiphilic monomers that include at least one fat chain; and
(6) copolymers of hydrophilic methacrylates or acrylates and hydrophobic monomers that include at least one fat chain.

11. The cosmetic composition according to claim 8, wherein the anionic amphiphilic polymers that include at least one hydrophilic unit and at least one unit having a fat chain are selected from the group consisting of compounds that include at least one allyl ether unit having a fat chain and at least one hydrophilic unit that is constructed from an ethylenically unsaturated anionic monomer, compounds that include at least one hydrophilic unit of the type of an olefinically unsaturated carboxylic acid and at least one hydrophobic unit exclusively of the type of an alkyl ($C_{1-30}$) ester of an unsaturated carboxylic acid, and methacrylic acid/methacrylate/dimethyl-meta-isopropenylbenzyl isocyanate copolymers of an ethoxylated alcohol.

12. The cosmetic composition according to claim 8, wherein the cationic amphiphilic polymers are selected from the group consisting of quaternized cellulose derivatives and polyacrylates having aminated side chains.

13. The cosmetic composition according to claim 8, wherein the amphoteric amphiphilic polymers that include at least one fat chain are selected from the group consisting of copolymers of methacrylamidopropyltrimethylammonium chloride/acrylic acid/alkyl ($C_{10-30}$) methacrylate.

14. The cosmetic composition according to claim 8, wherein the polysaccharides are selected from the group consisting of glucans, modified or unmodified starch compounds, amylose, amylopectin, glycogen, dextrans, celluloses and derivatives thereof, mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenins, agar-agar, glycosaminoglucans, gum arabic, tragacanth, ghatti gum, karaya gum, locust bean flour, galactomannans, xanthan gum, and mixtures thereof.

15. The cosmetic composition according to claim 1, wherein the thickening agent(s) are included in a total quantity from 0.001 to 20 wt % based on the total weight of the composition.

16. A method for treating keratinic fibers, comprising:
applying a hair treatment agent in accordance with claim 1 onto the keratinic fibers, and
rinsing the agent out again after a contact time from a few seconds to as much as 45 minutes.

* * * * *